United States Patent [19]
Green et al.

[11] Patent Number: 5,757,494
[45] Date of Patent: May 26, 1998

[54] SYSTEM AND METHOD FOR IMPROVING DATA ACQUISITION CAPABILITY IN SPECTROSCOPIC ELLIPSOMETERS

[75] Inventors: Steven E. Green; Craig M. Herzinger; Blaine D. Johs; John A. Woollam, all of Lincoln, Nebr.

[73] Assignee: J.A. Woollam Co. Inc., Lincoln, Nebr.

[21] Appl. No.: 422,346

[22] Filed: Apr. 14, 1995

Related U.S. Application Data

[63] Continuation-in-part of Ser. No. 327,107, Oct. 21, 1994, Pat. No. 5,582,640.

[51] Int. Cl.$^6$ ............................................. G01N 21/21
[52] U.S. Cl. ........................ 356/369; 356/365; 356/367; 250/225
[58] Field of Search ........................... 356/369, 367, 356/365; 250/225

[56] References Cited

U.S. PATENT DOCUMENTS

| | | | |
|---|---|---|---|
| 3,741,661 | 6/1973 | Yamamoto et al. | 356/117 |
| 3,880,524 | 4/1975 | Dill et al. | 356/118 |
| 4,053,232 | 10/1977 | Dill et al. | 356/118 |

(List continued on next page.)

OTHER PUBLICATIONS

Optics, Hecht, Addison–Wesley Publishing pp. 304–305, pp. 316–323.
Photonics Design & Applications Handbook, 39th Ed, 1993 pp. H–412–H–415.
Design and Operation of ETA, an Automated Ellipornetes. Havge & Dill, IBM J. of Research and Development, vol. 17, No. 6 pp. 471–554 Nov. 1973.
Regression Calibration Method for Rotating Element Elliprometer, Johs, Thin Solid Films, 234 (1993) pp. 395–398.
Meadowlark Optics Catalog Sheets Liquid Crsytal Retarder & p. 2, 3, 4, 5, 8 & 9.
Optics Girdes, Melles–Griot Catalog Sheets pp. 14–28–14–34.
Ellipsometry & Polarized Light, Azzan & Basheva, North–Holland pp. 152–181, pp. 245–267, pp. 399–416, pp. 370–373, pp. 405–416.

(List continued on next page.)

*Primary Examiner*—Frank G. Font
*Assistant Examiner*—Zandra V. Smith
*Attorney, Agent, or Firm*—James D. Welch

[57] ABSTRACT

The present invention is applicable generally to Spectroscopic Rotatable and Rotating Element Ellipsometers which utilize a relatively large range of wavelengths. Disclosed is a system and method for controlling the polarization state of a polarized beam of light so that it is in a range where the sensitivity of a Polarization State Detector used to measure changes in said polarized beam of light resulting from interaction with a Sample System, to noise and measurement errors etc., is reduced. Exemplified is a system, and method of use, for simultaneously setting both measured ellipsometric ALPHA, and ellipsometric BETA parameter values, (or equivalents), within ranges, in which ranges the sensitivity of transfer functions, and mathematical regressions which utilize said ellipsometric ALPHA and ellipsometric BETA values in the calculation of sample system characterizing PSI and DELTA constant values, to noise and errors in measurement etc., is found to be negligible. The present invention allows obtaining accurate and precise sample system PSI and DELTA Values from an Ellipsometer System in which a polarized beam of light is oriented at other than a Principal of Brewster Angle of Incidence to a sample system, allows determination of DELTA values in ranges otherwise not impossible, allows determination of the "Handedness" of a polarized beam of light, and provides means for determining all of Stokes Vector and Mueller Matrix component values. The present invention also provides means for making all system components added to a conventional ellipsometer system essentially end user transparent when desired, without removal thereof from said ellipsometer system.

31 Claims, 6 Drawing Sheets

U.S. PATENT DOCUMENTS

| | | | |
|---|---|---|---|
| 4,176,951 | 12/1979 | Robert et al. | 356/33 |
| 4,198,261 | 4/1980 | Busta et al. | 156/626 |
| 4,208,240 | 6/1980 | Latos | 156/627 |
| 4,407,709 | 10/1983 | Enjouji et al. | 204/192 |
| 4,408,884 | 10/1983 | Hleinknecht et al. | 356/355 |
| 4,758,304 | 7/1988 | McNeil et al. | 156/626 |
| 5,057,781 | 10/1991 | Atkins et al. | 324/635 |
| 5,076,696 | 12/1991 | Cohn et al. | 356/369 |
| 5,091,320 | 2/1992 | Aspnes et al. | 437/8 |
| 5,166,080 | 11/1992 | Schietinger et al. | 437/7 |
| 5,181,080 | 1/1993 | Fanton et al. | 356/381 |
| 5,276,503 | 1/1994 | Hayashi et al. | 356/369 |
| 5,311,285 | 5/1994 | Oshige et al. | 356/369 |
| 5,313,044 | 5/1994 | Massoud et al. | 219/121 |
| 5,329,357 | 7/1994 | Bernoux et al. | 356/369 |
| 5,335,066 | 8/1994 | Yanada et al. | 356/364 |
| 5,336,385 | 8/1994 | Shimose et al. | 204/298.03 |
| 5,373,359 | 12/1994 | Wollam et al. | 356/328 |
| 5,504,582 | 4/1996 | Johs et al. | 356/369 |

OTHER PUBLICATIONS

Recent Developments in Instrumentation in Elliprometry, Hague, Surface Science, vol. 96, 108, 140 (1980).

Automatic Rotating Element Ellipsonmeter: Calibration, Operation, and Real–time applications, Rev. Sci. Instrum. 61(8), Aug. 1990.

The Bereh Polarization Compensator, Model 5540 version Manual, New Fows Inc. Publication.

SYSTEM AND METHOD FOR IMPROVING DATA ACQUISITION CAPABILITY IN SPECTROSCOPIC ELLIPSOMETERS

The present Application is a Continuation-In-Part of application Ser. No. 08/327.107 filed Oct. 21, 1996, now U.S. Pat. No. 5,582,640, which discloses the use of other than a "Principal" or "Brewster" angle in Ellipsometer data acquisition.

TECHNICAL FIELD

The present invention relates to systems and methods for improving the data acquisition capability and operation of ellipsometer systems. Generally the present invention is a system and method for controlling the polarization state of a beam of polarized light in a spectroscopic ellipsometer, to place a measured ellipsometric ratio of "P" and "S" components, and a phase angle between said "P" an "S" components into ranges in which a polarization state detector is relatively insensitive to noise and measurement errors etc. therein. More particularly the present invention is a system, and method of use thereof, for simultaneously setting both measured ellipsometric ALPHA, and ellipsometric BETA ellipsometer parameter values, (or equivalents), within ranges, in which ranges the sensitivity of direct transfer functions or indirect mathematical regressions which utilize said ellipsometric ALPHA and ellipsometric BETA values, (or equivalents), in the determination of sample system characterizing PSI and DELTA constant values, to noise and errors in measurement etc., is found to be negligible. The present invention also allows obtaining accurate and precise data over a relatively large range of wavelengths, allows a polarized beam of light to be oriented at other than a Principal or Brewster angle of incidence to a sample system, allows determination of DELTA values in ranges thereof otherwise difficult, if not impossible to investigate, allows determination of the "Handedness" of a polarized beam of light, and provides means for determining all of Stokes Vector and Mueller Matrix component values. The present invention also provides means for making all system components added to a conventional ellipsometer systems essentially end user transparent when desired, without removal thereof from said conventional ellipsometer systems.

BACKGROUND

Spectroscopic ellipsometer systems for use in investigation and characterization of physical and optical properties of sample systems are well known. Briefly, such systems operate by monitoring changes effected in the polarization state of a beam of light when said beam of light is caused to interact with a sample system.

Spectroscopic ellipsometers systems typically comprise a Polarization State Generator, and a Polarization State Detector. In use, the polarization State Generator causes a beam of light in an intended state of polarization to be incident upon a sample system at a set Angle of Incidence (AOI), and the Polarization State Detector monitors a reflected and/or transmitted beam of light which emerges from said sample system and determines the polarization state thereof.

Continuing, spectroscopic ellipsometer systems fall into general categories such as:

a. Nulling Ellipsometers, (NE), (including automated versions (ANE);
a. Rotating Analyzer Ellipsometers (RAE);
b. Rotating Polarizer Ellipsometers (RPE);
c. Phase Modulation Ellipsometers (PME);
d. Rotating Compensator Ellipsometers (RCE);
e. Rotating Polarizer and Analyzer Ellipsometers (RPAE);
f. Rotating Polarizer and Analyzer, Fixed Compensator Ellipsometers (RPAFCE);
g. Rotating Analyzer and Compensator, Fixed Polarizer Ellipsometers (RACFPE);
h. Rotating Polarizer and Compensator, Fixed Analyzer Ellipsometers (RPCFAE);
i. Rotating Analyzer, Fixed Polarizer and Compensator Ellipsometers (RAFPCE);
j. Rotating Polarizer, Fixed Analyzer and Compensator Ellipsometers (RAFPE);
k. Rotating Compensator, Fixed Analyzer and Polarizer Ellipsometers (RCFAE);
l. Rotating Analyzer, Fixed Analyzer Ellipsometers (RAFAE);
m. Rotating Analyzer and Compensator, Fixed Analyzer and Polarizer (RACFAPE).

The catagorization is based upon what system components are present and how said system components are used. A review Article by Collins, Rev. Sci. Instrum. 61 (8), August 1990 provides a discussion of various ellipsometer configurations.

Generally, all ellipsometer systems include elements comprising:

a. a source of a beam of light;
b. means for imposing an intended state of polarization therein;
c. a means for analyzing said beam of light after it interacts with a sample system; and
d. a detector system for use in developing a signal from said beam of light after it interacts with said sample system, which signal contains information that allows determination of the optical and physical properties of said sample system.

While the present invention is applicable to essentially all of the identified types of spectroscopic ellipsometer systems which contain rotating elements, the present Disclosure will use as a non-limiting example, a J. A. Woollam Co. Inc. Variable Angle Spectroscopic Ellipsometer (VASE-13 Registered Trademark), (RAE) system. It is emphasized, however, that the general principals involved in the present invention are generally applicable to any spectroscopic ellipsometer system which contains rotating elements, examples of which were listed infra.

In more detail then, a spectroscopic Rotating Analyzer Ellipsometer (RAE) system comprises:

1. A Polarization State Generator (PSG) System, comprising:

a. a source of a beam of light, the wavelength of which beam of light can be set as desired by a user;
   b. a Polarizer (P) for use in setting a polarization state in said beam of light provided by said source of a beam of light.

2. A Polarization State Detector (PSD) System, comprising:

a. a Rotating Analyzer (RA), for use in processing said polarized beam of light after it interacts with a sample system, so that a linearly polarized beam of light of varying intensity is provided; and
   b. a Detector System (DET) for use in developing a signal from said beam of light after it emerges from said Rotating Analyzer (RA), which signal contains information which allows determination of the optical and physical properties of said sample system.

A typical procedure utilizing a conventional (RAE) system to determine the optical and/or physical properties of a sample system involves the steps of:

a. providing a beam of light of an intended wavelength from said source of a beam of light;

b. orienting said beam of light so that it approaches a present sample system (SS), the optical and/or physical properties of which are to be determined, at an Angle Of Incidence (AOI) near the "Principal" or "Brewster" angle for said Sample System (SS);

c. setting the Polarizer (P) to a known fixed position, so that its Azimuth is oriented so as to impose a desired state of polarization upon said beam of light;

d. causing said beam of light, after interaction with said sample system (SS) to pass through said Rotating Analyzer (RA) and emerge therefrom as a modulated, typically varying intensity with time, beam of light;

e. causing said typically varying intensity beam of light to enter a Detector System (DET), which Detector System (DET) produces a signal, the analysis of which allows determination of the optical and/or physical properties of the Sample System (SS).

Previous work by the J. A. Woollam Co. Inc. has determined that it is preferable to apply an elliptically polarized, (preferably essentially circularly polarized), beam of light to a Detector System (DET). This is because typical Detector Systems demonstrate undesirable polarization dependent sensitivity characteristics. That is, typical Detector Systems respond nonlinearly to different states of polarization, and thereby enter nonlinear Detector System errors to resulting calculated numbers which represent optical and/or physical properties. Said Detector System nonlinearity is, however, in typical Detector Systems, minimized when an essentially circularly polarized beam of light is applied thereto rather than linearly polarized beam of light, such as emerges from a Rotating Analyzer (RA). It is noted that linearly polarized light is converted to elliptically polarized light by passage through a Birefringent Retarder which serves to adjust the phase angle between well known "P" and "S" components in a polarized beam of light. (Note, "P" refers to that component of a polarized beam of light in a plane containing the normal to a sample system and the incident and reflected or transmitted beams, while "S" refers to that component perpendicular thereto, and parallel to the surface of said sample system).

Continuing, it is to be understood that the Rotating Element example (RAE) system described above, typically is best applied when a beam of polarized light is oriented so that it impinges upon a Sample System (SS) at the "Principal" or "Brewster" Angle Of Incidence (AOI), (note that the terms "Principal" and "Brewster" are used interchangably in this Disclosure), where the measured ellipsometer ellipsometric BETA parameter is essentially zero (0.0) and Sample System characterizing DELTA values are ideally near ninety (90) degrees. If the (AOI) is set away from the Brewster Angle, (which for semiconductors is approximately seventy-five (75) degrees), the quality of data obtainable from a (RAE) as described infra, without more, is degraded. The Brewster Angle thus sets a serious limitation on the utilizations of (RAE's). Prior work by the J. A. Woollam Co. Inc. has also determined that data obtained from a (RAE) in which the (AOI) is set in excess of the Brewster Angle, can, in some circumstances be of a quality to allow use in calculating Sample System PSI and DELTA values. Such is the topic in Copending patent application Ser. No. 08/327, 107 from which this Application is a CIP. However, the further away an (AOI) is from the Brewster Angle, the more difficult it is to obtain accurate and precise data. It should also be appreciated that the Brewster Angle depends on wavelength such that the ideal Angle Of Incidence (AOI) for one wavelength is not necessarily ideal at another. As a result, when a relatively large range of wavelengths is utilized it is necessary to adjust the Angle Of Incidence (AOI) to maintain a Brewster Angle. It would be very convenient if this (AOI) did not have to be so adjusted as utilized wavelengths are changed.

It would be also be of benefit if any (AOI) could be utilized in a Rotating Element Ellipsometer System without limiting the Spectroscopic capability thereof. For instance, the J. A. Woollam VASE (RAE) system operates over a range of from two-hundred-Thirty (230) to seventeen-hundred (1700) nanometers, but because of physical constraints imposed by real-time-in-situ Sample System Processing Systems to which the (VASE) is applied, it is not always convenient, or even possible, to set an appropriate Brewster (AOI) for a particular wavelength within said range. Restriction on possible (AOI's) then enter undesirable restrictions as to what wavelengths can be maximally utilized and still allow the obtaining of data of a sufficient quality to allow accurate calculation of Sample System characterizing PSI and DELTA values. Again, it would be of benefit if any (AOI) could be used with essentially any wavelength without degrading the capability of acquiring accurate and precise PSI and DELTA determining data.

As well, it is noted that typical Rotating Element Ellipsometers (REE's), such as described infra, are incapable of determining all the elements of a Stokes Vector or a Mueller Matrix for a sample system. (Stokes Vectors and Mueller Matracies are described in references such as the text titled "ELLIPSOMETRY AND POLARIZED LIGHT", by Azzam and Bashara, North-Holland, 1977, which reference is incorporated by reference into this Disclosure). To obtain all said elements it is required that one or more Retarders be placed between the Polarizer (P) and Rotating Analyzer (RA) in Rotating Analyzer Ellipsometer (REE) system, for instance, however, said Retarder(s) have an effect on the polarization state of a polarized beam of light, which effect is not always desired. (It is noted that similar use of Retarders is applicable in any Rotating Element Ellipsometer (REE)). However, in known (REE's) with such Retarder(s) present, undesired effects of said presence can not be conveniently avoided. That is, no known (REE) provides such Retarders in a manner such that they can be made to be essentially end-user "Transparent" by user adjustment. In known (REE) systems said Retarder(s) must be removed therefrom if the effects thereof are to be avoided. The ability to make on e or more Retarders present between a Polarizer (P) and an Analyzer (A) in a (REE) end user "Transparent" without removal thereof, would provide utility in the form of user convenience.

In addition, it is noted that a typical (REE) is incapable of determining the "Handedness" or direction of rotation of the polarization of a polarized beam of light used therein. It would be of benefit to be able to conveniently identify "Handedness".

Continuing, it is known in the practice of ellipsometry, to adjust the Azimuth Angle (POL) of a Polarizer (P) in a (RAE), (or the Analyzer in an (RPE)), system for instance, to adjust the value of a measured ellipsometric ALPHA to be within a range in which the sensitivity of a PSI Transfer function, (which is known to be a function of said ellipsometric ALPHA), to noise and errors in measurement etc. in measured ellipsometric ALPHA are made essentially negligible. It has not however, to the Inventor's knowledge, been possible to perform a related procedure to adjust ellipsometric BETA to optimum values, over a relatively large spectral range of wavelengths, (eg. two-hundred-thirty (230) to seventeen-hundred (1700) nanometers or greater).

It would be of great utility were it possible to adjust the measured value of ellipsometric BETA to be within a range in which the sensitivity of a DELTA determining transfer function, (which is known to be a function of ellipsometric ALPHA and ellipsometric BETA), to noise and measurement errors etc. in measured ellipsometric ALPHA and ellipsometric BETA is made essentially negligible. It would be especially convenient if such could be achieved by placing Retarder(s) between a Polarizer (P) and an Analyzer (A) in a (REE), such as required to allow obtaining full Stokes Vectors and Mueller Matrices setting, which Retarder (s) would allow setting a measured ellipsometric BETA value within a range in which DELTA Transfer function sensitivity to noise and errors in measurement etc. of ellipsometric BETA are made essentially negligible, emphasis added. (It is noted that where ellipsometric ALPHA and ellipsometric BETA are near zero (0.0) the modulation amplitude of detected intensity in an (REE) system is minimal).

In view of the above, it can be concluded that a system and method of its use which would allow precise accurate data to be achieved from an Ellipsometer System over a large, continuously variable, range of (AOI's) and wavelengths, and which would allow setting both ellipsometric ALPHA and ellipsometric BETA measured values in ranges wherein the sensitivity of PSI and DELTA Transfer functions, (which use as arguments said measured ellipsometric ALPHA and ellipsometric BETA), to noise and errors in measurement etc. in measured ellipsometric ALPHA and ellipsometric BETA are made essentially negligible, would be of great utility. It would be of further benefit if said system and method of its use could, as a natural consequence of the presence and utilization thereof respectively, be adapted to allow determination of all Stokes Vector and Mueller Matrix parameters. It would also be of utility if said system, adapted with elements added, could, by simple user adjustment be oriented so that added elements were made essentially end user transparent, thereby allowing use of an adapted Ellipsometer System in an essentially unadapted mode, without requiring that any elements be removed therefrom. It is emphasized that it would especially be of utility if said adapted Ellipsometer System could be conveniently utilized over a relatively large range of wavelengths.

A Search for relevant Patents which describe systems and/or methods which might be capable of providing the identified utility produced very little. In view of the fact that the present invention system, as is described supra in this Disclosure, in the Disclosure and Detailed description Sections, comprises Continuously Variable Retarder(s) (CVR's) placed between a Polarizer and Analyzer in a Spectroscopic Rotating Element Ellipsometer, which Continuously Variable Retarders (CVR's) are effective over relatively large spectral and Angle of Incidence ranges, the Search was focused upon systems which might be interpreted to provide said elements at said locations, or the equivalent effects thereof. Identified Patents are: U.S. Pat. No. 3,741,661 to Yamamoto et al.; U.S. Pat. No. 4,176,951 to Robert et al.; U.S. Pat. No. 5,181,080 to Fanton et al.; U.S. Pat. No. 5,311,285 to Oshige; U.S. Pat. No. 5,335,066 to Yamada et al. Also U.S. Pat. No. 4,053,232 to Dill et al; and U.S. Pat. No. 5,329,357 to Bernoux et al. were identified. None of said Patents are considered to be particularly relevant. However, another identified Patent, to Dill et al., U.S. Pat. No. 3,880,524, describes the use of a quarter-waveplate Compensator between a Polarizer and a Rotating Analyzer in a Rotating Analyzer Ellipsometer (RAE), such that the state of polarization of a reflected beam of light from a Sample System can be varied arbitrarily by merely adjusting the angular position (azimuths) of the Polarizer and said quarter-waveplate Compensator. Said quarter-waveplate Compensator can be placed ahead or after a Sample System. The system described in Dill et al. provides a means for adjusting both ellipsometric ALPHA and ellipsometric BETA in a polarized beam of light, which polarized beam is "monochromatic". No teachings as how to conveniently make said system applicable over a relatively large spectroscopic range of wavelengths, however, is present. Nor are any teachings found as how to make added system elements essentially end-user "transparent" at a desired wavelength without removal thereof from said Ellipsometer System. It is emphasized that the Dill et al. 524 Patent is to a monochromatic system, with no convenient provision for expanding to a relatively large spectral range without system element replacement. Also disclosed in an Article by Johs, titled "Regression Calibration Method For Rotating Element Ellipsometers, Thin Solid Films, 234 (1993). This article describes a regressions approach to calibration of rotating element ellipsometers, and is relevant to the present invention, as the present invention, in part, utilizes a mathematical regression procedure to indirect evaluation of PSI and DELTA Sample System Characterizing parameters.

There is then demonstrated a need for a convenient to use system and method for improving data acquisition capability of spectroscopic rotating element ellipsometers, which system and method can be conveniently utilized over a relatively large range of wavelengths and angles of incidence.

The present invention provides the identified utility.

DISCLOSURE OF THE INVENTION

The present invention is a system and method of use which allows obtaining accurate and precise data from Spectroscopic Ellipsometer Systems, over a relatively large range of wavelengths, and in which polarized light beams are not necessarily oriented at the Principal or Brewster Angle with respect to a Sample System (SS). Stated most generally, the present invention system and method allows changing the polarization state of a polarized beam of light so that Polarization State Detector sensitivity to noise and measurement errors is decreased. To accomplish the stated results the present invention allows controlling not only the measured ellipsometric relative magnitude ratio of the "P" and "S" components of a polarized beam of light during use, but also, simultaneously, the phase angle therebetween. (Note that the "P" component refers to that component which is in the plane containing the normal to a Sample System surface and the incident and reflected or transmitted beam(S) of light, and the "S" component is perpendicular thereto and parallel to the surface of a Sample System). For example, where Rotating Analyzer or Rotating Polarizer Ellipsometers are used, the present invention is a system and method of use which allows a user to set not only measured ellipsometric ALPHA, but also measured ellipsometric BETA values in ranges wherein Sample System (SS) characterizing PSI and DELTA Transfer function sensitivity to noise and errors in the measurement etc. of ellipsometric ALPHA and ellipsometric BETA is essentially negligible, (said PSI and DELTA Transfer functions being dependent upon said measured ellipsometric ALPHA and ellipsometric BETA values as demonstrated in the Detailed description Section of this Disclosure by presentation of relevant Transfer Function equations). The present invention allows accurate and precise determination of DELTA values in regions otherwise difficult, if not impossible, to investigate, and allows use of other than Principal or Brewster Angles. The present invention is also a system and method of use which allows the determination of elements in a Stokes Vector and a Mueller Matrix, and determination of the "Handedness" of a polarized beam of light utilized in said Ellipsometer System. The present invention system also allows a user to easily adjust elements added to a conventional Ellipsometer System, so that said added elements are essentially end-user transparent at any wavelength desired, thereby negating the need to remove said added elements from said present invention Ellipsometer System to allow use thereof in a conventional mode.

As described in the Background Section of this Disclosure, the present invention is applicable to any type of Ellipsometer System in which a Rotated or Rotating Element is present, (eg. Automated Nulling (ANE), Rotating Analyzer (RAE), Rotating Polarizer (RPE), Rotating Compensator (RC) and Rotating Analyzer and Polarizer Fixed Compensator (RAPFC), for instance). In the present Disclosure, however, only a Spectroscopic (RAE) will be used as an example. This exemplary usage is not to be interpreted as imposing any limitations on the scope of the present invention. (Note, as Jones and Mueller Matrix analysis of Rotating Element Ellipsometers reveals, similarities and symetries in the mathematics show that the practice taught in the present invention is quite general to the entire class of Rotating Element Ellipsometers (REE's) in general).

Continuing, a conventional Spectroscopic (RAE), such as the J. A. Woollam Co. Inc. Variable Angle Spectroscopic Ellipsometer (VASE—Registered Trademark), system is comprised of:

1. A Polarization State Generator System, (PSG), comprising:
   a. a source of a beam of light, the wavelength of which beam of light can be set as desired by a user;
   b. a Polarizer (P) for use in setting a polarization state in said beam of light provided by said source of a beam of light.

2. A Polarization State Detector System (PSD), comprising:
   a. a Rotating Analyzer (RA), for use in processing said polarized beam of light after it interacts with a Sample System (SS), so that a linearly polarized beam of light of typically varying intensity is produced; and
   b. a Detector System (DET) for use in developing a signal from said beam of light, after it emerges from said Rotating Analyzer (RA), which signal contains information which allows determination of the optical and physical properties of said Sample System (SS).

A conventional method of usage of such a Spectroscopic (RAE) system requires that the beam of light provided by the source of a beam of light be caused to pass through said Polarizer (P) to set a polarization state therein, then impinge upon the surface of a Sample System (SS) at an Angle Of Incidence (AOI) which is approximately the, wavelength dependent, Brewster Angle for said Sample System (SS). (Note that the Brewster Angle is that (AOI) at which the measured ellipsometric BETA is minimized and at which the Sample System (SS) characterizing DELTA parameter is approximately ninety (90) degrees). It is to be understood that the polarization state of said beam of light can be set by a user by rotation of the Polarizer (P) to set the Azimuthal Angle (POL) thereof, and also noted that each said Azimuthal Angle (POL) is associated with a specific value of the ellipsometer ellipsometric ALPHA value. It must be understood that said polarization state of said beam of light is changed by interaction with said Sample System (SS), and that the portion thereof reflected from said Sample System (SS) is caused to pass through said Rotating Analyzer (RA), thereby becoming a linearly polarized, typically varying intensity, modulated beam of light of altered polarization state, which then enters said Detector System (DET). Said Detector System (DET) serves to generate a signal from said entering beam of linearly polarized, typically varying intensity, modulated beam of light of altered polarization state, which generated signal can be subjected to Fourier Analysis, for instance, to provide measured values for ellipsometric ALPHA and ellipsometric BETA.

If, in the above procedure, the Angle Of Incidence (AOI) is not set near the Brewster Angle, for the wavelength of interest the quality of the data provided at the Detector System (DET) may be degraded. (Where glass is a Sample System, as little as one-tenth (1/10) degree variance can be significant, but where metal is a Sample System upwards of thirty (30) degrees variance from said Brewster Angle can be tolerable). It would be of great utility to be able to set the Angle Of Incidence (AOI) at essentially any value, apply a beam of light composed of any wavelength, and obtain precise and accurate data, thereby allowing calculation of Sample System (SS) characterizing PSI and DELTA values. The present invention enables such, by allowing a user to set the values of ellipsometric ALPHA and ellipsometric BETA in desired ranges.

To understand the present invention it is necessary to realize that a Birefringent Retarder can be oriented so as to effect "P" and "S" components of a polarized beam of light passing therethrough with different amounts of retardation. For instance, a linearly polarized beam of light passing through a Birefringent Retarder can be caused to become essentially circularly polarized by the effecting of an essentially ninety (90) degree retardation between one component, (ie. "P" or "S"), relative to the other. It is also to be understood that many types of Birefringent Retarders exist. One type, termed a "zero-order-waveplate" Retarder has its Optical axis in the plane of the surface thereof. Another type, termed a "Berek-type" Retarder has its Optical axis oriented essentially perpendicular to the plane of its surface. While both identified types of Birefringent Retarders can be used in the present invention system, the Berek-type Retarder is presently preferred. The reason for this present preference has to do more with "state-of-the-art" manufacture and availability than it does with physics of operation. Presently available Berek-type Retarders simply operate better in the present invention application.

It is also mentioned that Babinet and Soleil Double-Wedge-type; and Kerr and Pockels effect, and Liquid Crystal, electro-optic-type; and Voigt and Cotton-Mouton Magnetic-Faraday-effect Variable Retarders which can provide Variable Retardance over a relatively large range of wavelengths, can be used in the realization of the present invention. These alternative Variable Retarders are better describe din the Detailed Description Section of this Disclosure.

Now, as mentioned infra, it is known in the practice of Ellipsometry utilizing Rotating Analyzers, to adjust the Azimuthal Angle of a Polarizer (P) to set a measured ellipsometric ALPHA value within a desired range. In practice this is accomplished by setting a (POL) to a Sample System PSI value. However, until the present invention, it has not been possible to conveniently perform a similar maneuver on a measured ellipsometric BETA value over a relatively large wavelength range, (eg. two-hundred-thirty (230) to seventeen-hundred (1700) nanometers). To provide the identified utility, the present invention teaches that at least one Continuously Variable Retarder (CVR) should be placed in a Rotating Element Ellipsometer and specifically a Rotating Analyzer Ellipsometer System (RAE), (for example), between the Polarizer (P) and the Rotating Analyzer (RA), such that in use adjustment of said (CVR) allows setting a measured ellipsometric BETA value within a range in which DELTA Transfer Function sensitivity to noise and errors in measurement of ellipsometric BETA is reduced or minimized. A present invention system (CVR) can be placed ahead of and/or after a Sample System (SS), within the teachings of the present invention. In use, a method of operation will then include a step in which a present Continuously Variable Retarder (CVR) is adjusted to set a value of ellipsometric BETA, simultaneous with adjustment of ellipsometric ALPHA by the adjustment of a Polarizer (P), so that both ellipsometric ALPHA and ellipsometric BETA are in desired ranges for optimal accuracy and precision of data. For other Rotating Element Ellipsometers, such as (RPE), (RPAFCE) etc. complimentary procedures are followed.

It should be understood that adjustment of said (CVR), positioned in an Ellipsometer System as described, allows, within the range of operation of said (CVR), setting a ellipsometric BETA value to near zero (0.0). This is the case whether the Angle Of Incidence (AOI) of the polarized beam of light incident on the Sample System (SS) is set to the Brewster Angle or not. This is significant because it adds a degree of freedom to a user of an Ellipsometer System fitted with the present invention system. Said degree of freedom being the ability to utilize an (AOI) greatly removed from the Brewster Angle, and still obtain high quality data from which accurate DELTA, (and PSI), values can be obtained.

It is noted that it is not unknown to place Fixed or Variable Retarders between a Polarizer (P) and Rotating Analyzer (RA) in an Ellipsometer System. Variable retarders have been placed ahead of, and/or after, Sample Systems (SS) in past practice to allow evaluation of all Stokes Vector and Mueller Matrix elements.

What has not previously been possible, however, is the ability to adjust said so-placed (CVR) elements in a Spectroscopic Rotating Element Ellipsometer (REE) System, so as to set measured ellipsometric BETA values in a desired range, over a relatively large range of wavelengths, (eg. two-hundred-thirty (230) to seventeen-hundred (1700) nanometers or greater).

Perhaps the reason the present invention use of a (CVR) has been overlooked until now is that, as alluded to infra, presently commercially available zero-order-waveplate-type Variable Retarders are not capable of performing ellipsometric BETA value settings over a significant spectroscopic wavelength range without introducing a significant amount of unwanted artifacts on a Primary Polarized Beam of light Polarization State. In addition it must be understood that three such zero-order-waveplate-type (CVR's) are required in series to provide a continuously variable retardance capability over the range of zero (0.0) to ninety (90)degrees, when a wavelength range of two-hundred-thirty (230) to seventeen-hundred (1700) nanometers is covered. This is because wavelengths which are multiples of other wavelengths are present in said relatively large range of wavelengths, and if less than three zero-order-waveplate Retarders are present, then at some wavelength, the retardation effected will become one-hundred-eighty (180) degrees, which corresponds to simply changing the orientation of a polarization component, rather than introduction of a usable retardation of an elliptical nature, to a polarized beam of light, at said wavelength. If only one such zero-order-waveplate is utilized, it must be changed to cover a spectroscopic range. (That is, individual zero-order-waveplates are manufactured specifically for, and applicable for use at only one wavelength). Also, if an Ellipsometer System is to be used in a mode wherein the zero-order-waveplate-type (CVR's) presence is not detectable, the zero-order-waveplate-type (CVR's) must be physically removed from said Ellipsometer System. This is extremely end-user inconvenient, requiring possible recalibration of the retardance each time such a retarder is introduced, and also requiring expensive and complicated connect and disconnect mounting apparatus be present in an ellipsometer system.

The present invention avoids the problem identified when presently commercially available zero-order-waveplates-type (CVR's) are used, by, in the preferred embodiment, utilizing presently commercially available Berek-type (CVR's). A Berek-type (CVR) has its Optical Axis in a plane essentially perpendicular to the surface thereof. In use, instead of rotation, as is required where zero-order-waveplate (CVR's) are utilized, Berek-type Retarders are "tilted", and said "tilt" can be imposed about multiple axes. (Note that this would be equivalent to rotating a zero-order-waveplate-type Retarder simultaneously in clockwise and counterclockwise directions. That is, at least two such zero-order-waveplate-type Retarders would necessarily have to be present and in series with one another). The present invention utilizes two mutually perpendicular "tilt" axes, termed Azimuthal and Elevational by the Inventors. A very important property of said presently commercially available Berek-type (CVR's) for use in Rotating Element Ellipsometers (REE), is that a one-plate, two surface system is capable of providing retardation of the range from zero (0.0) to in excess of ninety (90) degrees over a large range of wavelengths (eg. two-hundred-thirty (230) to seventeen-hundred (1700) nanometers where a presently available J. A. Woollam Co. Inc. VASE is utilized). (A Berek-type Retarder can be oriented for use at a desired wavelength by setting a "Tilt" thereof. That is, a manufactured Berek-type Retarder is not specifically manufactured for use at one wavelength, or over but a small band of wavelengths, as are zero-order-waveplates, but by user orientation thereof can be set so as to be usable at any wavelength, over a large range of wavelengths).

The present invention system then, in one preferred embodiment, adds at least one Berek-type (CVR) between a Polarizer (P) and a Rotating Analyzer (RA) in a Spectroscopic Rotating Analyzer Ellipsometer to allow user control of a measured ellipsometric BETA value between one (1.0) and zero (0.0) in use. It should be appreciated that a DELTA of ninety (90) degrees is the ideal, and that corresponds to a ellipsometric BETA value of zero (0.0), but that said ideal is not an absolute requirement to improve the operation of an Ellipsometer. Any reduction in the measured value of ellipsometric BETA allows improved precision and accuracy in measured data. Rotating Element Ellipsometer Systems without the present invention are inherrantly incapable of measuring accurate DELTA Values near zero (0.0) and near one-hundred-eighty (180) degrees. As will be demonstrated in the Detailed description Section of this Disclosure, with the present invention Berek-type (CVR) present, the "quality" of measured ellipsometric BETA value data are such that DELTA's near both zero (0.0) and one-hundred-eighty (180) degrees can be precisely and accurately determined therefrom. As well, as will be demonstrated in the Detailed Description Section of this Disclosure, highly precise and accurate data can be achieved where an Angle Of Incidence (AOI) greatly removed from the Brewster Angle is used, when the present invention system is present and utilized, and this is true over a large spectroscopic range of wavelengths.

Another benefit realized by the use of presently commercially available Berek-type (CVR's) is that multidirectional "tilt" capability provided thereto by the present invention system allows a user to precisely adjust the Berek-type Retarder so that a polarized beam of light passing therethrough is essentially unaffected, except for possibly a negligible attenuation. This allows a user to, without disassembling an Ellipsometer System and removing a present invention (CVR), configure an Ellipsometer System fitted with the present invention (CVR) system, as if said present invention (CVR) was not present. This provides great end-user convenience in practice.

The present invention also teaches that PSI and DELTA Sample System (SS) characterizing parameters can be calculated by an indirect mathematical regression approach applied to a data set which comprises a plurality of measured ellipsometric ALPHA and ellipsometric BETA values, (or equivalents), obtained when different (CVR) settings are utilized. For instance, as presented in the Detailed Description Section of this Disclosure, tests have been run where two (2) Polarizer Angles (POL's) are utilized, with five (5) (CVR) "Tilts" being set for each (POL). It will be appreciated that ten (10) measured ellipsometric ALPHA-ellipsometric BETA pairs are provided by this example. It is also to be understood that any number of (POL's) and (CVR) "tilts", (eg. other than the two (2) (POL's) and five (CVR) "tilts" identified above), can be utilized, and be within the spirit of the present invention.

Of course, as is well known, the presence of two (CVR's) placed ahead of and after a Sample System (SS), respectively, will allow evaluation of all Stokes Vector and Mueller Matrix elements.

As well, the "Handedness" of a polarized beam of light can be determined by noting the effect a present invention (CVR) has thereon.

The present invention will be better understood by reference to the Detailed description Section of this Disclosure with reference being had to the accompanying Drawings.

SUMMARY OF THE INVENTION

In the most general sense, it is a primary purpose of the present invention to provide a system for controlling the polarization state of a polarized beam of light in an Ellipsometer System, such that a measured ellipsometric magnitude ration of "P" and "S" components, and a measured ellipsometric phase angle between said "P" and "S" components are simultaneously set within ranges in which a Polarization State Detector System has reduced sensitivity to noise and errors in the measurement thereof, such that Sample System PSI and DELTA Constants can be more accurately and precisely determined from said measured ellipsometric ratio of "P" and "S" components, and measured ellipsometric phase angle between said "P" and "S" components.

It is another purpose of the present invention to provide Rotating Element Ellipsometers with a system providing users the capability of setting not only ellipsometric ALPHA, but also ellipsometric BETA values within desired ranges in use, such that determination of PSI and DELTA Sample System characterizing constants, obtained by direct application of transfer functions to measured ellipsometric ALPHA and ellipsometric BETA, or by indirect mathematical regression applied to an array of ellipsometric ALPHA and ellipsometric BETA data pairs, is essentially immune to noise and errors in measurement etc. of said ellipsometric ALPHA and ellipsometric BETA, thereby allowing determination of DELTA values in ranges otherwise difficult or impossible to investigate, (ie. near zero (0.0) and near one-hundred-eighty (180) degrees.

It is still yet another purpose of the present invention to teach that presently commercially available Berek-type Retarders should be mounted so as to enable multiple axes of "tilt", rotation around which a user can control, such that a Berek-type Retarder added to an Ellipsometer can be adjusted to essentially eliminate the effects of its presence, any imperfections therein and/or modify a State of Polarization in a polarized beam of light which passes therethrough during use, as desired by a user.

It is yet still another purpose of the present invention to teach that presently commercially available systems of multiple zero-order-waveplate-type Retarders in series, as well as Babinet and Soleil-type Variable Retarders, and electro-optical-effect-type Kerr and Pockel and Liquid Crystal Variable Retarders, and magnetic-faraday-effect Voigt and Cotton-Mouton Retarders should be mounted in Rotating Element Ellipsometers so as to enable modification of a State of Polarization, as described, in a beam of polarized light which passes therethrough during use.

It is another purpose of the present invention to teach that addition of a system which allows setting a measured ellipsometric BETA value within a user desired range, allows operation of a rotating Element Ellipsometer at Angles of Incidence, (of a Polarized Beam of Light with respect to a Sample System), other than the Brewster Angle, while enabling the gathering of precise and accurate data from which can be calculated PSI and DELTA Sample System characterizing Constants.

It is yet still another purpose of the present invention to teach a system for meeting the above recited purposes, which is spectroscopic and can be used with polarized beams of light over a relatively large range of wavelengths.

It is still yet another purpose of the present invention to provide a system which can be utilized to determine all the elements of a Stokes Vector and a Mueller Matrix.

It is another purpose of the present invention to teach a system which can be utilized to determine the "Handedness" of a polarized beam of light in a Ellipsometers.

It is still another purpose of the present invention to meet the above stated purpose by addition of a system to Ellipsometers which can be user adjusted to appear end-user "Transparent" when desired, without any disassembly of and removal of elements from said Rotating Element Ellipsometers.

It is additionally a purpose of the present invention to teach methods of use of Ellipsometers, to which the system of the present invention has been added, which methods of use allow the above cited purposes associated with the system of the present invention, to be achieved.

DETAILED DESCRIPTION

Figure 1:
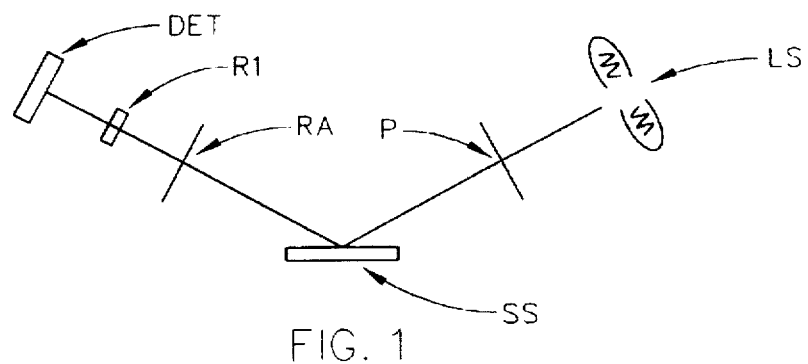
FIG. 1 shows a Variable Angle Spectroscopic Ellipsometer (VASE—Registered Trademark), System.

The present invention can be used with essentially any Spectroscopic Ellipsometer System which contains one or more Rotatable or Rotating Elements.

In the most general sense the present invention is a system and method for controlling the polarization state of a polarized beam of light utilized in an Ellipsometer system. The present invention system and method allows a user to simultaneously set a measured ellipsometric relative magnitude ration of "P" and "S" components, as well as a measured ellipsometric phase angle between said "P" and "S" components in a polarized beam of light. (Note that the "P" component is that component of a polarized beam of light in a plane defined by a normal to a Sample System surface, and the incident and reflected or transmitted beams, while the "S" component is perpendicular thereto and parallel to the surface of the Sample System). The purpose of controlling said polarization state of said polarized beam of light is to cause said measured ellipsometric relative magnitude ration of "P" and "S" components, and said measured phase angle between said "P" and "S" components to be in ranges in which a Polarization State Detector demonstrates decreased sensitivity to noise and errors in measurement etc. thereof. Said present invention system and method allows determining Sample system Characterizing PSI and DELTA Constants, in ranges otherwise difficult, if not impossible, to investigate. For instance, well known Sample System characterizing DELTA values can be obtained near zero (0.0) and one-hundred-eighty (180) degrees. As well, Angles of Incidence (AOI's) far removed from a Brewster Angle can be utilized.

(Note that "P" and "S" components and PSI and DELTA are defined and derived in the Text titled "ELLIPSOMETRY AND POLARIZED LIGHT", By Azzam and Bashara, North-Holland, 1977, which text is incorporated by reference in this Disclosure).

As a specific example, the J. A. Woollam Co., Inc. Variable Angle Spectroscopic Ellipsometer (VASE—Registered Trademark), allows application of a Polarized Beam of Light of One (1) Wavelength at a time to a Sample System (SS), at one Angle of Incidence (AOI) at a time. In use, various (AOI's) are utilized, as are various Wavelengths at said various (AOI's), to acquire a Data Set, use of which allows calculation of Sample System PSI and DELTA Characterizing parameter Constant Values. (Note that different PSI and DELTA Constant Values are associated with each (AOI) and Wavelength). In addition, note that typical technique requires that an Angle Of Incidence (AOI) near an optimum (AOI), (termed the Brewster Angle, or Principal (AOI), see supra), be utilized with a Sample System under investigation, to assure the acquisition of a Data Set which is of a precision and accuracy that allows reliable calculation of Sample System (SS) characterizing PSI, and especially DELTA, Constant Values therefrom. Depending upon the Sample System being investigated, deviations from the Brewster Angle can be permissible, but where, for instance, glass is investigated, said tolerable deviation might be as small as one-tenth (1/10) a degree. Where metals are investigated tolerable deviations can be upwards of thirty (30) degrees.

In addition, the J. A. Woollam Co. manufactures M-44, and M-88 etc. Rotating Analyzer Ellipsometer (RAE) Systems which allow simultaneously application and analysis of a multiplicity (eg. forty-four (44) or eighty-eight (88) etc.), of Wavelengths in a Polarized Beam of Light. While the present invention was developed utilizing a (VASE) System, it can in some instances also be applied to the M-44 and M-88 etc. systems. One said instance involves in-situ-real-time data acquisition from Sample System (SS) processing systems in which an Ellipsometer System can not be interfaced to said processing system in a manner which allows a beam of polarized light from said Ellipsometer System to impinge upon said Sample System (SS) at near the ideal, well known, Brewster Angle, or Principal Angle Of Incidence (AOI).

Continuing, Ellipsometers, (Rotating Analyzer Ellipsometer (RAE) Systems being used as an example herein), operate by detecting the change in polarization State caused in a Beam of Polarized Light, when said Beam of Polarized Light is caused to interact with a Sample System (SS).

Briefly, as shown in FIG. 1, for reference purposes, a basic J. A. Woollam Co. Rotating Analyzer Ellipsometer (RAE) VASE System comprises:

1. A Polarization State Generator System (PSG) comprising:

a. a Source of a Beam of Light, which Beam of Light can typically comprises a multiplicity of wavelengths, which wavelengths are utilized one at a time;

b. a Polarizer (P) which serves to set a desired state of polarization in said beam of light by adjustment of the Polarizer Angle (POL) thereof;

c. a Means for causing said Polarized Beam of Light to interact with a Sample System, (ie. a means to set an Angle Of Incidence (AOI).

2. A Polarization State detector System (PSD) comprising:

a. a Rotating Analyzer (RA) which serves to process said Polarized Beam of Light after it interacts with said Sample System (SS), such that a typically Modulated Intensity, essentially Linearly Polarized beam of Light, is produced;

b. a Detector System (DET) which measures the Intensity waveform of said resulting Elliptically Polarized typically Modulated Intensity waveform as a function of time.

(Note, a Retarder (R1) is also shown as present in FIG. 1. Said Retarder (R1) is typically not present in a J. A. Woollam Co. Inc. (RAE) VASE Ellipsometer system, and is discussed supra with regard to the J. A. Woollam Co. Inc M-44, or M-88 (RAE) Ellipsometer System in which said (R1) Retarder is commonly employed).

It is to be understood then that an Ellipsometer System, in use, can be considered to be comprised of a Polarization State Generator System, (PSG), a Substrate System, (SS), and a Polarization State Detector System, (PSD), where all components preceding the Sample System (SS) are lumped together under the term "Polarization State Generator System (PSG)" and all components after the Sample System (SS) are lumped together under the term "Polarization State Detector System (PSD)". Thus, in the above recitation, Components identified as 1a, 1b, and 1c are considered to be part of the (PSG) and the Components identified in 2a, 2b, and 2c, are considered to be part of the (PSD).

Next, it is to be understood that the intensity waveform of an elliptically polarized beam of light entering a Rotating Analyzer Ellipsometer (RAE) Detector System (DET), as a function of time, is characterized by a mathematical equation which involves well known measurable Ellipsometric ALPHA and BETA parameters in a trigonometric relationship, with the Azmuthal Angle of said Rotating Analyzer being the argument of said trigonometric functions. See EQ 1. Equation 1 provides definitions for ellipsometric ALPHA and BETA.

$$I=io(1+ALPHA\ COS(POL)+BETA\ SIN(POL)) \qquad \text{EQ. 1}$$

where "A" is the Rotating Analyzer Azimuth Angle. (Note that EQ. 1 also applies to a Rotating Polarizer Ellipsometer wherein the angle "A" is replaced with a similar angle "P" which corresponds to a Rotating Polarizer Azimuth Angle). (It is to be noted that EQ. 1 can be satisfied by any number of ellipsometric ALPHA and ellipsometric BETA value pairs. That is, there is not but a single unique pair of ellipsometric ALPHA and ellipsometric BETA values which satisfy EQ. 1. If, for instance, one arbitrarily sets an ellipsometric ALPHA value, (which can be accomplished by adjusting the Polarizer (P) Polarization Angle (POL) by a adjustment of said Polarizer in said (PSG)), evaluation of EQ. 1 in view of a Detector provided set of Data will provide an accompanying ellipsometric BETA value, but such an ellipsometric ALPHA-BETA pair will exist for each (POL) setting a user cares to set).

While not a focus of the present invention, previous activity by the J. A. Woollam Co. has determined that for their "M-44" and M-88" (RAE's) the Retarder (R1) identified in FIG. 1 is best be placed after the Rotating Analyzer and ahead of the Detector System (DET) so that the essentially linearly polarized beam of light which emerges from the Rotating Analyzer during use is converted to an elliptically polarized beam of light, (ideally a circularly polarized beam of light), prior to entry to said Detector. Again, this is because most Detectors, (in a Polarization State Detector System (PSD)), are less prone to introduce Polarization Dependent Sensitivity errors into Polarized Light Beam Intensity measurements when an entering polarized beam of light is elliptically, (preferably essentially circularly), polarized than when it is linearly polarized. (Note that circular polarization refers to the state wherein the well known "P" (parallel to a plane of incidence defined by a perpendicular to an investigated sample system surface and the incident and reflected or transmitted beam(s)), and "S" (parallel to the surface of said sample system and perpendiclar to said "P" component), components of a polarized beam of light are at ninety degrees with respect to one another, and linear polarization refers to a state in which said P and S components are in phase). Particularly where a Diffraction Grating is present in a Detector System, (but not limited to said case), it has been found that Detector Polarization Dependence Sensitivity of a Detector can be greatly reduced by application of an essentially circularly polarized Beam of Light thereto, as compared to the result when a linearly polarized beam of light is so applied. Previous Patent Applications (eg. Ser. Nos. 08/265,325 and 08/339,834), submitted by the J. A. Woollam Co. focus on this use of Retarders in a Rotating Analyzer Ellipsometer system. (Note, if multiple wavelengths are utilized, said Retarder might be Variable to allow an optimum Retardance to be set for each as it is utilized, but in general, for the purposes of this Disclosure, said Retarder for minimizing Detector polarization dependent sensitivity can be considered as Fixed).

Now, the present invention, in its preferred embodiment, makes use of one or more Retarder(s), (eg. Variable Retarder (s)), (see FIG. 2 (VR1) & (VR2)), but for a very different purpose and in a very different manner than Retarder (R1).

It is to be understood that a Variable Retarder can be applied in a system in such a way that the amount of Retardation provided thereby is Continuously Variable. That is, a Variable Retarder can be oriented in a system so as to have essentially no effect on a polarized beam of light passing therethrough, (other than perhaps an essentially negligible minor attenuation effect on the intensity thereof), or it can be oriented in a system to effectively convert linear polarization to essentially circular polarization, (that is, provide ninety (90) degrees of Retardation to the "P" relative to the "S" component in a polarized beam of light and vice versa), or it can provide other amounts of Retardation, greater or lesser than Ninety (90) degrees. For instance, a Berek-Type Variable Retarder, (see supra), can be placed in an Ellipsometer System and positioned such that a polarized beam of light has an angle of incidence (AOI) of zero (0.0) degrees to the Optical Axis thereof, (which Optical Axis is, ideally, perpendicular to the surfaces of said Berek-Type Variable Retarder), so that the polarization state of said polarized beam of light is not effected by the presence of said Berek-type Retarder. However, if the Berek-Type Variable Retarder is "Tilted" so that the Beam of polarized light has an angle of incidence (AOI) other than zero (0.0) degrees to the Optical Axis thereof, the polarization state, (ie. the angular relationship of the "P" and "S" components with respect to one another), of said polarized beam of light can be greatly effected. Greater angles of "Tilt" will effect an impinging polarized beam of light with effectively greater retardation. It is noted that Berek-Type Variable Retarders can provide continuously variable amounts of Retardation over a large range of wavelengths as well. That is, unlike zero-order-waveplates, Berek-type Retarders are not designed for use at but a single wavelenght, (or at best a small band of wavelenghts around an average design-wavelength). This makes said Berek-type Retarders especially attractive in the context of the present invention.

Figure 4A:
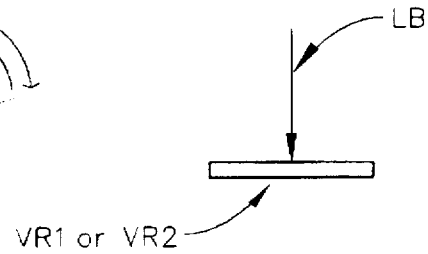
FIG. 4a shows a Retarder with a light beam incident thereon perpendicular to the surface thereof.
Figure 4B:
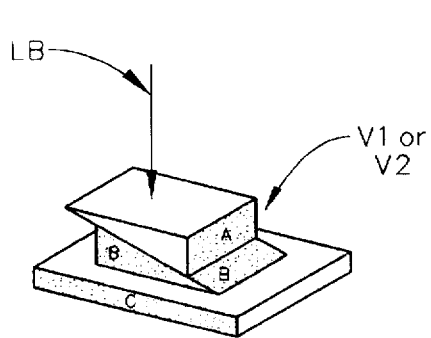
FIG. 4b shows Babinet and Soleil-type Variable Retarders Systems.
Figure 4C:
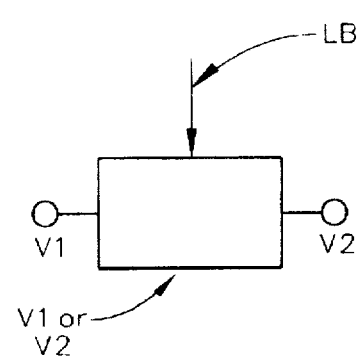
FIG. 4c indicates electro-optical-effect Kerr, Pockel and Liquid Crystal-type Variable Retarders, as well as magnetic-Faraday-effect Voigt and Cotton-Mouton-type Retarders.

In addition to Berek-type Variable Retarders, it is also possible to utilize Liquid Crystal, Kerr, Pockels, Babinet and Soleil Variable Retarders and systems of multiple seriesed zero-order-waveplate-type Retarders, (see supra) as Continuously Variable Retarders. Said various types of Variable Retarders are well known by those skilled in the art of Ellipsometry, and will be but briefly described herein. First, Liquid Crystal Variable Retarders are true zero-order retarders in which the Retardance effected on a polarized beam of light changes with a voltage applied thereto. Next, Kerr and Pockels Variable Retarders are both electro-optical-type Variable Retarders which become Birefringent when an electric field is applied thereto. FIG. 4c provides representation of Kerr, Pockel and Liquid Crystal Variable Retarders generally. (Note it is not primarily a geometrical shape which serves as a Kerr, Pockel and Liquid Crystal Variable Retarders basis of operation, but rather the effects the application of electrical fields and voltages exert on the birefringence nature of materials from which they are constructed, hence the rather simple representation of FIG. 4c). Induced Birefringence is proportional to the square, and linearly, to applied Electric fields in Kerr and Pockels Variable Retarders, respectively. Also available are Variable Retarders which operate based upon application of a magnetic field. FIG. 4c is again used as a representation thereof, where V1 and V2 are considered to be an applied Magnetic Field. Examples of such "magnetic-faraday-effect" Variable Redarders are Voigt and Cotton-Mouton systems. Said Variable Retarders provide Birefringence proportional to the square of an applied magnetic field. Continuing, Babinet and Soleil Variable Retarders are each comprised of two wedges, the angled faces of which are placed into slidable contact with one another. As said wedges are caused to move with respect to one another, the effective thickness encountered by a beam of light passing therethrough at a fixed location with respect thereto changes. Said change in effective thickness changes the amount of birefringent retardation effected thereby. Reference to FIG. 4b demonstrates that Soleil Variable Retarders also have an essentially nonvariable Retarder in series with the two-wedge Variable Retarder system. The Optical axes, (eg. (A) and (B)), of the two wedges in a Babinet Variable Retarder are typically oriented at ninety (90) degrees with respect to one another, while in a Soleil Variable retarder said optical axes are oriented in-line with one another, (eg. (A) and (B')), while the essentially nonvariable Retarder optical axis (C) is oriented at ninety (90) degrees with respect thereto. The above identified alternative Variable Retarders are well known and can be applied to the present invention in addition to Berek-type and multiple zero-order waveplate-type Retarder Systems. The criteria for application being that a Retarder System can be made operable over a relatively large range of wavelengths, (eg. they are usable in a spectroscopic ellipsometer system which operates over, for instance, the range of two-hundred-thirty( (230) to seventeen-hundred (1700) nanometers or greater). It is also to be understood that the terminology, (eg. Berek, Babinet, Soleil, Kerr, Pockles, Liquid Crystal, Voigt and Cotton-Mouton etc.) is to be interpreted broadly rather than limiting, to Variable Retarders which operate functionally as described. That is, Berek refers to Variable Retarders with an optical axis perpendicular to the surface thereof, while zero-order-waveplate Variable Retarders refer to those with an optical axis parallel to the surface thereof. Babinet and Soleil are to be interpreted as identifying any Variable Retarders of dual wedge construction. Kerr, Pockles and Liquid Crystal are to be interpreted to identify any Variable Retarders which operate based upon electro-optical effects and Voigt and Cotton-Mouton are terms which are to be interpreted to identify any Variable Retarders which operate based upon magnetic-effects. FIGS. 4a, 4b and 4c each show a Light Beam (LB) impinging thereon.

Regarding Rotating Analyzer Ellipsometers (RAE's), it is to be understood that well known practice is to determine ellipsometric ALPHA and ellipsometric BETA as defined in EQ. 1, in view of a Detector System (DET) provided Measured Intensity vs. Time Data Set. (Note that "A", the Rotating Analyzer Azmuthal Angle in Eq. 1 which is the argument of the COS and SIN Trig Functions, is a function of time). Multiple D.C. measurements can also form a Data Set which can be utilized in determination of ellipsometric ALPHA and ellipsometric BETA, (eg. a select set ellipsometric ALPHA and ellipsometric BETA Values corresponding to a number of Azimuthal angular settings of "A").

Ellipsometric ALPHA and ellipsometric BETA are generally, but not necessarily, found by a "Fourier Analysis" approach as applied to an appropriate Data Set obtained at a Detector System (DET) in an Ellipsometer System. Some procedures then apply mathematical corrections to the so-determined ellipsometric ALPHA and ellipsometric BETA parameters to provide ellipsometric ALPHA PRIME and ellipsometric BETA PRIME parameters in an attempt to minimize the effects of Polarization Dependence Sensitivity, electrical signal gain in amplifiers and the like. Other mathematical manipulations can also be performed.

However, whether mathematical manipulation of the measured ellipsometric ALPHA and ellipsometric BETA is done or not, the purpose of determining the ellipsometric ALPHA and ellipsometric BETA parameters in Rotating Element Ellipsometers (REE's) is generally to allow the mathematical calculation of well known Sample System (SS) Characterizing Ellipsometer PSI and DELTA Constant parameters by means of Transfer Functions. Said PSI and DELTA Constant parameter values being representative of an investigated Sample System (SS) optical properties, (eg. such as refractive index, extinction coefficient and even temperature), and for instance, of the thickness and composition of a thin film(s) present on the surface of a Sample Substrate. The conversion of measured ellipsometric ALPHA and ellipsometric BETA parameters to calculated PSI and DELTA values is by means of well known Transform Equations. See Eqs. 2 and 3 for the equations which apply to (Rotating Analyzer Ellipsometer (RAE) systems:

$$TAN(PSI) = \frac{\sqrt{1+ALPHA} \; ABS(TAN(POL))}{\sqrt{1-ALPHA}} \quad \text{EQ. 2}$$

$$PSI = ARCTAN\left(\frac{\sqrt{1+ALPHA} \; ABS(TAN(POL))}{\sqrt{1-ALPHA}}\right)$$

$$COS(DELTA) = \frac{BETA}{\sqrt{1-ALPHA^2}} \quad \text{EQ. 3}$$

$$DELTA = ARCCOS\left(\frac{BETA}{\sqrt{1-ALPHA^2}}\right)$$

where (POL) is an angle set by a Polarization State Generator, (see description of a Rotating Analyzer Ellipsometer System infra), which is easily controlled by a user. As the angle (POL) is changed, it will be observed from Eq. 3 that the measured value of ellipsometric ALPHA involved in arriving at a Sample System Constant PSI Value will change. For other (REE's) similar equations exist. For example in (RPE) systems, the angle (POL) in Eqs. 2 and 3 is replaced by an angle (ANL), the Azimuthal angle of an Analyzer.

(Note. Equations 1 and 2 are derived in standard texts on Ellipsometer. such as "ELLIPSOMETRY AND POLARIZED LIGHT" by Azzam and Bashara, North Holland, 1977, and discussed in a Review Article by Collins, title "AUTOMATIC ROTATING ELEMENT ELLIPSOMETERS: CALIBRATION, OPERATION, AND REAL-TIME APPLICATIONS:, REV. SCI. INSTRUM. 61 (8) AUGUST 1990. These references are incorporated by reference into this Disclosure.)

Observation of Eq. 2 shows that an ellipsometric ALPHA value of approximately one (1.0) will cause the equation denominator to go to zero (0.0), and the value provided by said equation for any set Polarization State Generator Polarizer, Polarizer (P) set Angle (POL), to be infinity. Such a result defeats the goal of Ellipsometric Analysis. If, however, ellipsometric ALPHA is approximately zero (0.0) then Eq. 2will be sensitive to changes in the Polarization State Generator (PSG), Polarizer (P) set Angle (POL), and not ellipsometric ALPHA. This is a desirable situation as noise and errors in measurement etc. of ellipsometric ALPHA value are eliminated while the Polarization State Generator (PSG), Polarizer (P) set Angle (POL) remains controllable by a user. Now, it is known that different settings of the Polarization State Generator (PSG), Polarizer (P) set Angle (POL), are associated with different values of ellipsometric ALPHA. That is, a user controlling the Polarization State Generator (PSG), Polarizer (P) set Angle (POL) can effect a desired Detector System (DET) measured value of ellipsometric ALPHA. As indicated, ideally one would want ellipsometric ALPHA to be zero (0.0), however, it will be noted that any ellipsometric ALPHA value below about nine-tenths (0.9) will serve to greatly reduce the effect of noise and errors in measurement etc. in ellipsometric ALPHA, in the calculation of PSI via Eq. 2. That is, while preferable, it is not absolutely required that the value of ellipsometric ALPHA be zero (0.0) to sufficiently decrease the sensitivity of Eq. 2 to changes in ellipsometric ALPHA such as can occur because of noise, or because of errors in measurement or determining ellipsometric ALPHA by evaluating to EQ. 1 in view of a measured Detector provided Data Set, for instance. (That is, Data can be obtained which can be utilized in Calculating PSI and Delta Values when ellipsometric ALPHA is not zero (0.0), even though that is an optimum Value for ellipsometric ALPHA).

As was alluded to infra, it is well known, in (RAE) systems, to adjust the Polarization State Generator Angle (POL) to set a desired ellipsometric ALPHA value in practice. What has not been possible, prior to the present invention, however, is the ability to conveniently provide control of ellipsometric BETA values, over a relatively large range of wavelengths, (eg. two-hundred-thirty (230) to seventeen-hundred (1700) nanometers), for a similar reason as described with respect to ellipsometric ALPHA. (Note that similar procedures are applicable in other (REE's)). Inspection of Eq. 3 shows that calculation of DELTA, (again a Sample System (SS) characterizing parameter which is constant for a given (AOI) and Wavelength), requires knowing a measured parameter ellipsometric BETA. It occurs, in certain ranges of ellipsometric BETA parameter values, that ellipsometric BETA is very sensitive to unavoidable noise and measurement errors etc. introduced in conducting an investigation of a Sample System (SS). Hence, just as is the case with ellipsometric ALPHA, it would be desirable to be able to control the value of ellipsometric BETA so that it is in a range where the effect of noise and errors in measurement etc. ellipsometric BETA, in the Eq. 3 transfer function which provides DELTA, are negligible. As with ellipsometric ALPHA, a value of zero (0.0) is ideal, but not absolutely required.

To date no known system and method has been available to allow convenient ellipsometric BETA Value range control capability over a relatively large spectroscopic range of wavelengths, emphasis added.

There is thus demonstrated a need for a system and method that will allow a user to adjust an Ellipsometer System during use, such that both measured ellipsometric ALPHA and ellipsometric BETA parameter values can be simultaneously set to values in ranges wherein noise and errors in measurement thereof etc. have negligible effect on the calculation of PSI and DELTA by Transfer Function Eqs. 2 and 3. As noted with respect to Eq. 1 infra, numerous pairs of ellipsometric ALPHA-ellipsometric BETA values can satisfy EQ. 1. Some values of ellipsometric ALPHA, (ie. near zero (0.0) or at least less than nine-tenths (0.9)), however, will be found to decrease the sensitivity of Eq. 2 to noise and measurement errors etc. in ellipsometric ALPHA as compare to that present when greater Values of ellipsometric ALPHA are utilized. As well, some relatively low values of ellipsometric BETA will decrease the sensitivity of Eq. 3 to noise and measurement errors in ellipsometric BETA. If a user could then adjust an Ellipsometer System so that Eqs. 2 and 3 are provided ellipsometric ALPHA and ellipsometric BETA Values nearer zero (0.0) than to one (1.0), said ellipsometric ALPHA and ellipsometric BETA Values being arrived at by, for instance Fourier Analysis, in view of a set of Data obtained experimentally from said Detector System (DET), then said Ellipsometer System provided data would be made insensitive to noise and errors in measurement etc. in arriving at ellipsometric ALPHA and ellipsometric BETA values, as said noise and errors in measurement effect calculation of PSI and DELTA values from Eqs. 2 and 3. The present invention provides a system and method for allowing control over the measured ellipsometric BETA value, in addition to the measured value of ellipsometric ALPHA.

Figure 2:
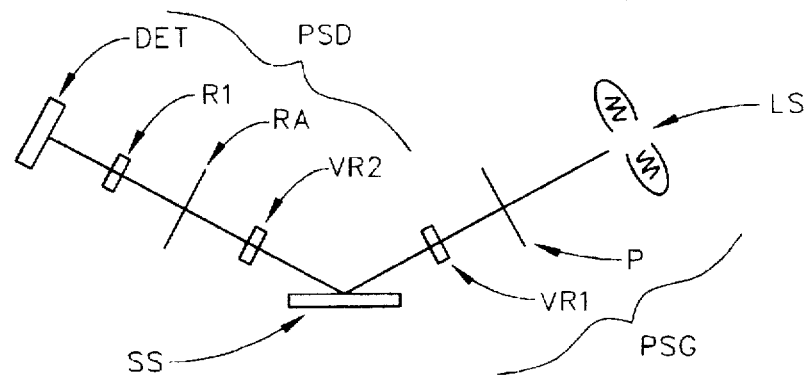
FIG. 2 shows the typical Variable Angle Spectroscopic Ellipsometer (VASE) System of FIG. 1 with Variable Retarders added between the Polarizer and Rotating Analyzer.

The present invention can be most easily understood by reference to FIGS. 1 and 2. As mentioned infra, FIG. 1 shows a typical J. A. Woollam Co. Variable Angle Spectroscopic Rotating Analyzer (RAE) Ellipsometer, (VASE) System which is being used as an example Ellipsometer system herein. Shown are a Light Source (LS) which provides a beam of light, a Polarizer (P), a Sample System (SS), a Rotating Analyzer (RA) a Retarder (R1) and a Detector System (DET). FIG. 2 shows the system of FIG. 1 with added Variable Tilt Retarders (VR1) and (VR2). As described above, said Retarder (R1) is positioned after the Rotating Analyzer (RA) and ahead of the Detector System (DET) and serves to reduce the effect of Polarization Dependence Sensitivity of a Detector System (DET) in use. However, Variable Retarders (VR1) and (VR2) are placed head of the Rotating Analyzer (RA). (Note, (VR1) is present in the Polarization State Generator System (PSG), and (VR2) is present in the Polarization State Detector System (PSD)). In use both said Variable Retarders (VR1) and (VR2) can be present, or only one thereof might be present. The point is that the presence of a Variable Retarder at the location of (VR1) and/or (VR2) allows a user an adjustment by which the measured ellipsometric BETA parameter value can be set. While it is not unknown to place Variable retarders in Ellipsometer Systems such as shown in FIG. 2, the use made thereof disclosed herein is, within the knowledge of the Inventors, new. Known uses of Variable Retarders placed as are (VR1) and (VR2) are, for instance, to effect circular polarization on a Polarized Beam of Light in the vicinity of the Sample System, (so that, for instance, all Stokes Vector and Mueller Matrix components can be measured, see Azzam and Bashara reference cited infra). In the present scenario, however, such is not the primary purpose and it will be appreciated that once the Polarized Beam of Light passes through the sequentially following Rotating Analyzer (RA), it will again be Linearly Polarized.

Continuing, reference to Eq. 4 shows the effect of (VR1) and/or (VR2).

$$COS(DELTA + R) = \frac{BETA}{\sqrt{1 - ALPHA^2}} \qquad Eq. 4$$

$$DELTA = ARCCOS\left(\frac{BETA}{\sqrt{1 - ALPHA^2}}\right) - R$$

where "R" is the amount of Retardation provided by (VR1) and/or (VR2). (Note, EQ 4 is technically value only where the fast axis of the Variable Retarder is in the "P" or "S" plane, however, said equation generally demonstrates the effect utilized by the present invention).

Comparison to Eq. 3 shows that the argument of the COS term has been modified by the addition of the Retardation effected by the presence of (VR1) and/or (VR2). Alternatively, it can be stated that an "Offset" is added to the Equation for calculating DELTA by the "Tilt" of (VR1) and/or (VR2), thereby effecting a change of the value of the measured ellipsometric BETA parameter. Again, said measured value can be set to be, ideally, near zero (0.0), although any reduction in a measured value thereof is beneficial.

In use a routine which allows measuring an ellipsometric ALPHA and ellipsometric BETA pair solution to EQ. 1, (typically as arrived at by Fourier Analysis of a Data Set provided experimentally at the Detector System (DET)), will be followed. Said routine provides an ellipsometric ALPHA value in a range which is not significantly sensitive to noise and errors in measurement etc. involved in arriving thereat, so that in application of Eqs. 2, (which it will be recalled allows calculation of PSI from a measured ellipsometric ALPHA value), the effect of noise and errors in measurement and etc. of ellipsometric ALPHA are negligible. As well, said routine allows setting a measured ellipsometric BETA Value in a range in which it is not significantly sensitive to noise and errors in measurement etc. thereof.

Figure 3A:
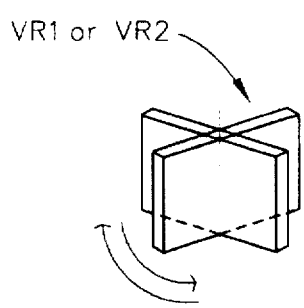
FIGS. 3a and 3b, show Azimuthal and Elevational "Tilts" respectively which can be applied to Berek-type Variable Retarders, when such comprise the Variable Retarders shown in FIG. 2.
Figure 3B:
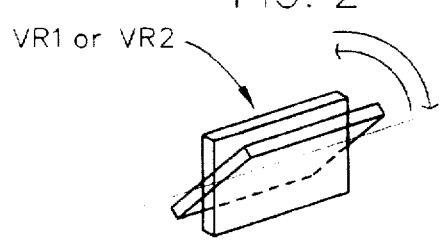

Now, it will be appreciated that Retarders (VR1) & (VR2) can each physically constitute a Plate of a finite thickness, presenting with offset essentially parallel surfaces. (Note, however, that no Retarder is physically perfect). Such a Plate can be "Tilted" in many ways. Two preferred axes of rotation are demonstrated in FIGS. 3a and 3b. FIG. 3a shows Azimuthal Tilt around a Vertical Axis and FIG. 3b shows Elevational Tipping around a Horizontal Axis. Note that both Clockwise and Counterclockwise Rotations can be effected in both the Azimuthal and Elevational cases. Such mutlidirectional Tilt adjustment capability allows adjusting-out the effect of imperfections, which vary from Retarder to Retarder, in the context of an Ellipsometer System. (For instance, one imperfection which occurs is that the optical Axis of a Retarder is oriented other than exactly perpendicular or parallel to the surface of the Retarder. The ability to effect multidirectional "tilting" of such a retarder allows matching the (AOI) of an impinging Beam of Light essentially "exactly" as desired with respect to the actual direction of the Polarization Axis of a Retarder. This capability, as far as the Inventors know, has not previously been available in an Ellipsometer System).

It is also noted that a preferred Retarder, the general nature of which was described directly infra, is a Berek-Type Magnesium Fluoride Plate with a bandwidth of operation in excess of the two-hundred-thirty (230) to seventeen-hundred (1700) nanometers utilized in the Rotating Analyzer Ellipsometer System being described, (eg. a VASE System), which Berek-Type Magnesium Fluoride Plate provides an effective Retardance, variable over a range of from zero (0.0) to in excess of plus or minus ninety (90) degrees, over said entire range of frequencies for two-hundred-thirty (230) to seventeen-hundred (1700) nanometers. (Note that Saphire might also a usable material from which a Berek-Type Retarder can be made as is Mica. Mica, however, becomes opaque in certain wavelength regions of interest. As well, Quartz, even though being Optically active in that it rotates a Polarized Beam of Light, is also a possible material for a Berek-type Retarder). It is noted that preferred Berek-Type Magnesium Fluoride Plates are available from New Focus, Inc., and are identified by Part No. Berek Polarization Compensator 5540.

FIG. 4a shows a Beam of Light incident upon a Berek-type Retarder Plate at a an Angle of Incidence (AOI) of zero (0.0) degrees thereto, (ie. the angle between the normal to the surface of the Retarder Plate and the impinging Beam of Light is zero (0.0) degrees). In an ideal Berek-Type Retarder the Optical axis is perpendicular to the plane of the surface (s) of the Retarder plate, and the Polarization State of a Polarized Beam of Light which is aligned with the Optical Axis so as to impinge at said ninety (90) degree angle to said surface(s), is not significantly affected as it passes therethrough. In practice, the Optical Axis of a Berek-Type Retarder can be slightly off perpendicular to the surface of thereof, and the surfaces thereof may not be exactly parallel to one another, but a multidirectional tilting procedure can be utilized to effect coincidence between the direction of the Polarized Beam of Light and the actual effective Optical Axis. Said multidirectional tilting procedure will generally be found to be require different amounts of tilt for each specific Berek-Type Retarder because of manufacturing variance from one unit to another.

It is noted that Retarders with an Optical Axis parallel to the surface thereof, (zero-order-waveplates), could possibly be used in the present invention, instead of Berek-type Retarders, but a problem with doing so with presently commercially available systems exists as such systems do not simply apply a direct amount of retardation to a Polarized Beam of Light to effect, for instance, a variable zero (0.0) to ninety (90) degree retardation. Rather, two plates are typically involved in commercially available zero-order-waveplate Retarder Systems which have the Optical Axis parallel to the surface. Said systems are designed such that one plate, for instance, effects a five-thousand (5000) degree retardation in one direction of rotation, and a second plate provides a four-thousand-one-hundred-ten degree retardance in the opposite direction of rotation. The end effect on a Polarized Beam of Light exiting the described System then is an introduced of retardation to a Primary Polarized Beam of an intended ninety (90) degrees. In addition, it has been found that presently Commercially available Retarders with the Optical Axis in the plane of the Surface thereof, (eg. zero-order waveplates), are used, multiple such systems in sequence are required to effect a Variable Retardance over the entire range of zero (0) to ninety (90) degrees, over a relatively large spectroscopic range of wavelengths, (eg. two-hundred-thirty (230) to seventeen-hundred (1700) nanometers and greater). This results because over a relatively large spectroscopic range of wavelengths, which range includes therein wavelengths which are half as long as others in said relatively large spectroscopic range, a fixed zero-order-waveplate Retarder will serve only to provide one-hundred-eighty (180) degrees of retardation at said half wavelength lengths. That is it will simply rotate the orientation of a linearly polarized wave rather than provide it with any elliptical influence. (It is noted that to provide a full zero (0.0) to ninety (90) degrees of Retardation at all wavelengths in the identified spectroscopic range of wavelengths, requires three (3) fixed zero-order-waveplate Retarders in series to avoid the identified one-hundred-eighty (180) degree "rotated orientation" sign problem).

It is noted that any system which allows sufficient user control of Retardance over the identified relatively large spectroscopic range of wavelengths can be used in the present invention. Numerous possible types of Variable Retarders were identified herein infra. However, for the present, Berek-Type Retarders are preferred as problems in the use thereof have been found to be minimal, as compared to problems encountered when, for instance, multiple presently commercially available zero-order-waveplates are utilized.

It is also noted that the presence of a Variable Retarder (VR1) and/or (VR2) as shown in FIG. 2 allows determination of the direction of rotation, (the "Handedness") of a polarized Beam of Light. Introduction of a Retardation "R" will effect the Polarization State by adding to, or subtracting from an existing Polarization State, depending on the "Handedness" thereof. By detecting the direction of the effect of adding Retardance "R", one knows the "Handedness" of the Polarized Beam of Light acted upon. "Handedness", it is noted, is otherwise not determined by an Ellipsometer System. Prior to the present invention "Handedness" has been determinable in an ellipsometer which has been effectively converted to a polarimeter by: obtaining a set of ALPHA and BETA values, entering a ninety (90) degree Retarder into the ellipsometer/polarimeter system, and obtaining a second set of ALPHA and BETA values. The present invention allows utilizing other than ninety 90) degrees retardance when obtaining the second set of ALPHA and BETA values. "Handedness" is described in a paper by Hauge and Dill titled "Design and operation of ETA, an Automated Ellipsometer", IBM J. of Dev. and Research, Vol. 17, No.6, November 1973, which reference is incorporated by reference in this Disclosure. As well, the presence of a Retarders in the position of (VR1) and (VR2), in combination with a Rotating Analyzer in an Ellipsometer System allows determination of all the elements of a Stokes Vector if said Retarder is caused to "Tilt—for Berek-type Retarder" or "rotate—for zero-order-waveplate". This is yet another benefit of the presence of a Retarder (VR1) and/or (VR2) as shown in FIG. 2. (Note, VR2 must be present to determine a Stokes Vector). Also, with the presence of Retarders (VR1) and (VR2) in the positions shown, if both are "tilted" or rotated during use while the Analyzer (RA) and Polarization State Generator (PSG) are held stationary, determination of all sixteen (16) elements of the Mueller Matrix is possible. The meanings of the terms "Stokes Vector" and "Mueller Matrix" are well known in the field of Ellipsometry and Polarimetry and will not be further discussed here. An article titled "Recent Developments In Instrumentation In Ellipsometry", by Hauge, Surface Science, Vol. 96, No. 108, 1980 describes Stokes Vectors and Mueller Matrices and said reference is incorporated by reference in this Disclosure.

Figure 4D:
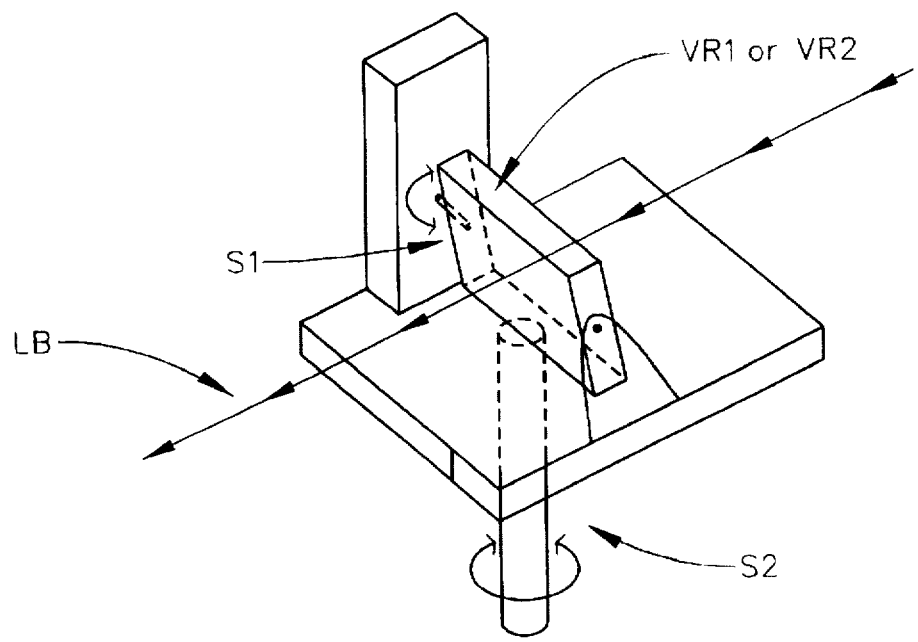
FIGS. 4d and 4e show multi-tilt Berek-type Variable Retarder systems.
Figure 4E:
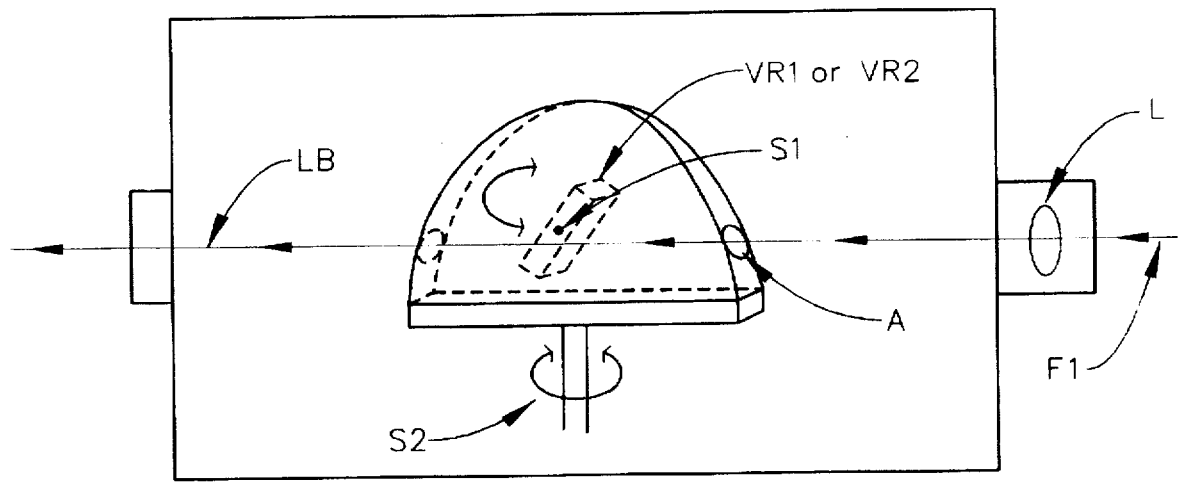

Various modes of operation of Ellipsometer systems as shown in FIGS. 1 and 2, without, and fitted with the present ellipsometric BETA control Retarder(s) (VR1) and/or (VR2), respectively, present in view of FIGS. 3a, 3b and 4a–4e. FIG. 4a–4c were discussed infra. FIGS. 3a and 3b show two axes of "Tilt" of a Berek-type Variable Retarder (VR) such as utilized in the exemplary J. A. Woollam Co. Inc. VASE Rotating Analyzer Ellipsometer (RAE) System utilized in this Disclosure to obtain the results demonstrated in FIGS. 5a–5d, 6, and 7a–7f, discussed supra. FIGS. 4d and 4e show Rotation of said Berek-type Variable Retarder (VR) around mutually perpendicular shafts (S1) and (S). Shown also is a Light Beam (LB) passing through said Berek-type Variable Retarder (VR) FIGS. 4d and 4e. FIG. 4e provides another view of a two axes of "tilt" Berek-type Variable Retarder (VR) with a Light Beam (LB) passing therethrough. FIG. 4e also shows a Fiber (F1) carrying said Light Beam (LB) to Focusing Lens (L). Said Light Beam (LB) is shown passing through a Berek-type Variable Retarder (VR) via an aperture (A) in a housing therefore.

A Case 1 No-Plate Mode refers to a scenario in which neither Variable retarder (VR1) or (VR2) is present, and in which the Polarizer (P) is adjusted to set ellipsometric ALPHA in an insensitive range and a resulting ellipsometric ALPHA-ellipsometric BETA pair is directly provided from the Detector System (DET) Data, typically by a Fourier Analysis procedure applied to modulated intensity data in (REE's).

A Case 2 No-Plate Regression Mode refers to a scenario in which neither Variable Retarder (VR1) or (VR2) is present, and in which a number of Polarizer (P) settings are effected and a Data Set comprised of a number of ellipsometric ALPHA-ellipsometric BETA pairs, provided by analysis of data provided by the Detector System (DET), are mathematically subjected to a regression procedure to determine optimum PSI and DELTA Values in view thereof. This approach to PSI and DELTA evaluation does not impose any control on the value of ellipsometric BETA, however, this approach to determining PSI and DELTA is itself considered by the Inventors to be new, novel, nonobvious and useful, without more.

A Case 3, Plate-Zero-Mode is identified wherein an ideal Berek-Type Variable Retarder (VR1) and/or (VR2) is/are present, as shown in FIG. 2. Said Berek-type Variable Retarder(s) has/have the optical Axis thereof oriented perpendicular to the surface thereof. It the beam of light is incident along the Optical Axis of said Berek-type Variable Retarder Plate, as shown in FIG. 4a, then except for minor attenuation, the Variable Retarder Plate has no effect. Thus an Ellipsometer system can include such a Berek-Type Variable Retarder Plate which need not be physically removed when not used in certain instances. Simple alignment will make its presence essentially undetectable, thereby making use of the Ellipsometer System much more convenient. (Note, multiple "Tilt" direction capability allows orienting the Berek-type Variable Retarder so that its presence is end-user Transparent at any wavelength over the large range of at least two-hundred-thirty (230) to seventeen-hundred (1700) nanometers). This convenience, to the inventor's knowledge, has not here-to-fore been available in any ellipsometer system where Variable Compensators are present.

Two Cases, in addition to the above mentioned Case 3 Plate-Zero-Mode, apply to an Ellipsometer System in which Variable Retarder(s) (VR1) and/or (VR2) is/are present.

The Inventors define a significant Case 4 VASE-C MODE. FIGS. 5 through 7, (discussed supra), show results obtained using this Mode of operation. In the specific tests demonstrated in said Figures, two (2) (RAE) Polarizer Angle (POL) positions were used, and Five (5) Variable Retarder positions were used at each thereof, leading to a collection of Ten (10) data ellipsometric ALPHA-ellipsometric BETA pair values. The Five Variable Retarder Positions correspond to Zero (0.0) Tilt, a Clockwise and a Counter-Clockwise Azimuthal Tilt and a Clockwise and a Counterclockwise Elevational Tilt, (see discussion with respect to FIGS. 3a and 3b infra). (Note that forty-five (45) degree Tilts were utilized to acquire the data which was utilized to calculate the PSI and DELTA values plotted in FIGS. 5–7). A Mathematical Regression was applied to said ten (10) ellipsometric ALPHA-ellipsometric BETA pair data to find Constant PSI and DELTA parameters which provide the best fit by a minimized Square Error approach. (Said Regression Procedures are well known to those knowledgeable in the field of Ellipsometry. The most commonly used version goes by the name "Marquardt-Levenberg" and involve standard non-linear techniques of equation parameter evaluation). It is to be noted that in this case some of the ten (10) ellipsometric ALPHA-ellipsometric BETA pairs will not have ellipsometric ALPHA and/or ellipsometric BETA values which are in ranges which are insensitive to noise and errors in measurement etc., but application of the Mathematical Regression approach to evaluating PSI and DELTA in view of the plurality of ellipsometric ALPHA-ellipsometric BETA pair data, provides a result which is surprisingly good, emphasis added. (Note, it is to be understood that the use of Ten (10) ellipsometric ALPHA-ellipsometric BETA pairs was arbitrary and that other numbers of ellipsometric ALPHA-ellipsometric BETA pairs could be used by changing the number of (AOI's) and number of Retarder "Tilt" positions so as to arrive at other than ten ellipsometric ALPHA-ellipsometric BETA parameter values for use in the Regression evaluation of PSI and DELTA). It is noted that the only difference between Case 2 and Case 4 is that in Case 4, a ellipsometric BETA affecting Retarder Plate present in the Ellipsometer System and is utilized as a means to control measured ellipsometric BETA values while collecting ellipsometric ALPHA-ellipsometric BETA pair data. That is Case 2 also utilizes a Mathematical Regression approach to arriving at PSI and DELTA.

A Case 5 Plate-Mode refers to a scenario in which ellipsometric ALPHA is set to a value in a range where it is insensitive to noise and measurement errors etc. by adjustment of the Polarizer, and ellipsometric BETA is set to a value in a range where it is similarly insensitive by adjustment of Variable Retarder(s) (VR1) and/or (VR2). Then as in Case 1, Fourier Analysis, (or some similar technique), is applied to data acquired from the Detector System (DET) to evaluate an ellipsometric ALPHA and a ellipsometric BETA. The only difference between Case 1 and Case 5 is that in Case 5 a ellipsometric BETA affecting Retarder Plate is present in the Ellipsometer System and utilized to set ellipsometric BETA to an insensitive region value in use.

Figure 5A:
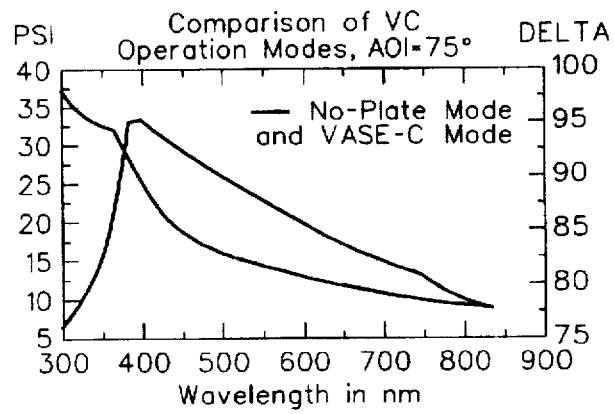
FIGS. 5a through 5d show plots of Sample System characterizing PSI and DELTA values as a function of wavelength of light utilized in a beam of polarized light, applied to a Sample System at seventy-five (75) and at thirty (30) degrees Angles of Incidence, as arrived at by various Modes of operation.
Figure 5B:
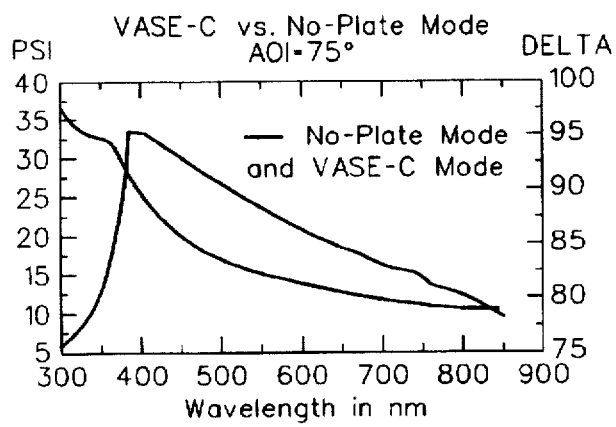
Figure 5C:
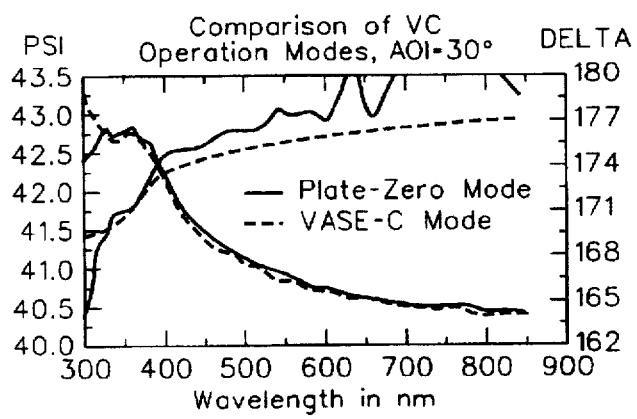
Figure 5D:
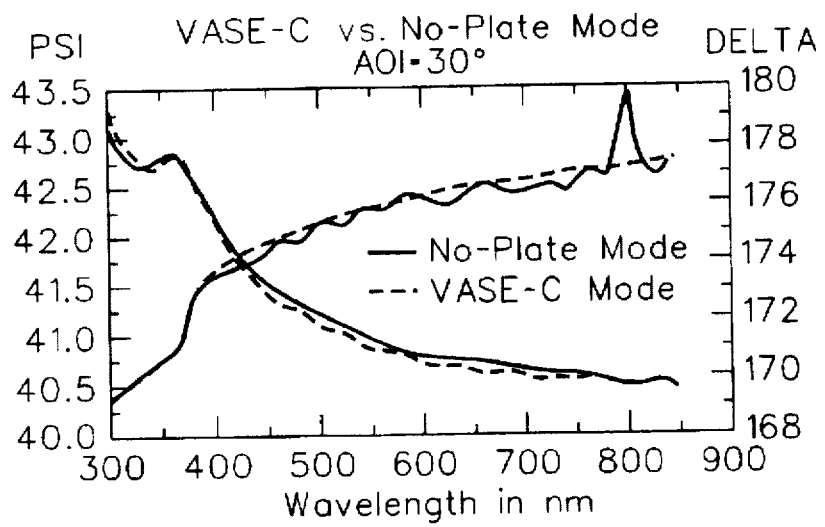
Figure 6:
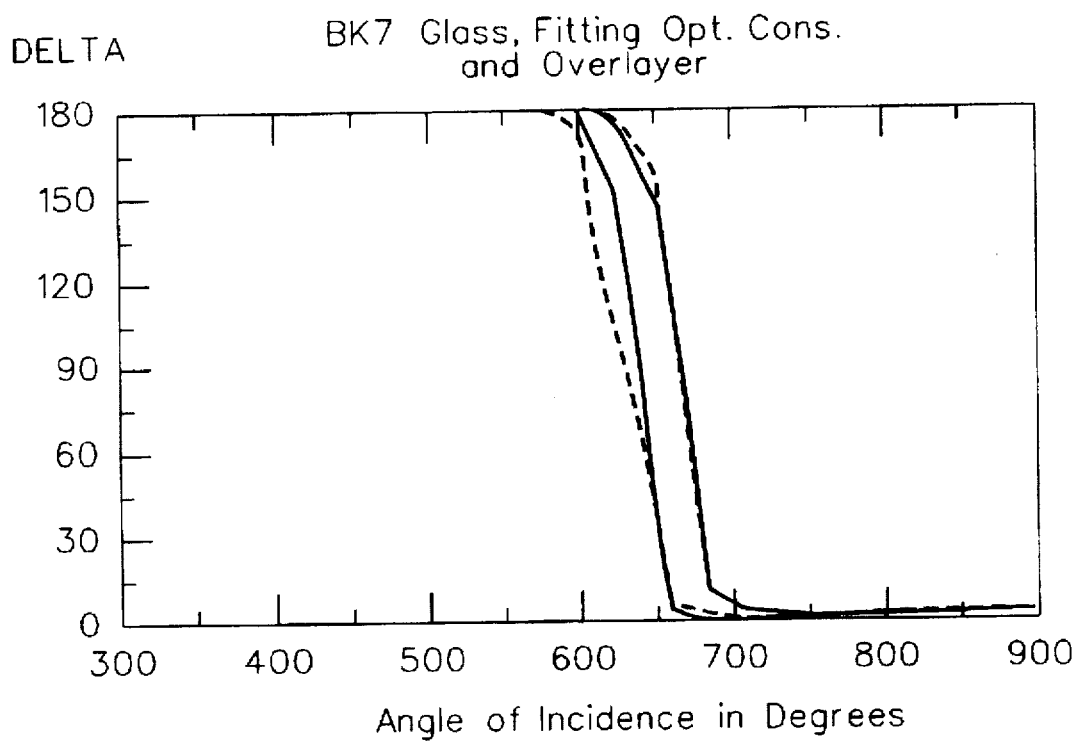
FIG. 6 shows DELTA values as a function of the Angle of Incidence of a beam of polarized light to a Thick Glass Sample System, said DELTA values being determined by a present invention operation Mode method.

FIGS. 5a and 5b demonstrate PSI and DELTA plots achieved from data acquired where an (AOI) of seventy-five (75) degrees was utilized. FIG. 5a shows a comparison between Case 3 Plate-Zero Mode and Case 4 VASE-C data and FIG. 5b shows a comparison between Case 1 No-Plate Mode and Vase-C mode. Note that at a seventy-five (75) degree (AOI) all modes provide good PSI and DELTA data. FIGS. 5c and 5d show plots achieved from data acquired similarly to how data was acquired for the plots in FIGS. 5a and 5b respectively, but where an (AOI) of thirty (30) degrees. Note that only the Case 4 VASE-C mode provides good Delta Data.

FIG. 6 shows DELTA calculated from data achieved from data acquired by investigating Thick BK7 Glass using a Case 4 VASE-C Mode where the (AOI) was varied from fifty (50) to sixty-two (62) degrees. Note that reliable DELTA values are achieved near zero (0.0) and one-hundred-eighty (180) degrees, where reliable values for DELTA are not ordinarily obtainable. (It will be recalled that an (AOI) near the Principal or Brewster Angle must typically be utilized to allow obtaining reliable values for DELTA, and said reliable values are then near ninety (90) degrees).

Figure 7A:
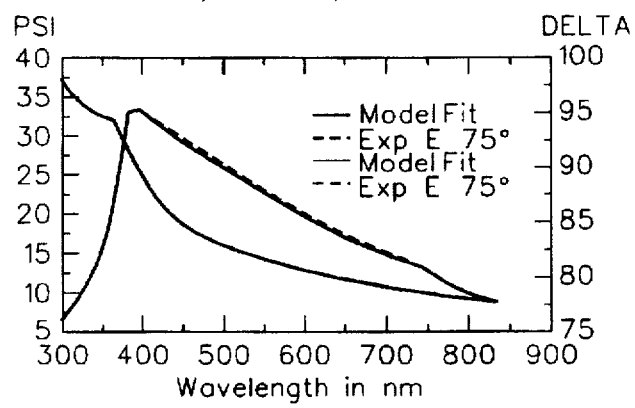
FIGS. 7a through 7f show plots of Sample System characterizing PSI and DELTA values as a function of wavelength of light utilized in a beam of polarized light, applied to a Sample System at seventy-five (75) and at thirty (30) degrees Angles of Incidence, as arrived at by various Modes of operation of the ellipsometer.
Figure 7B:
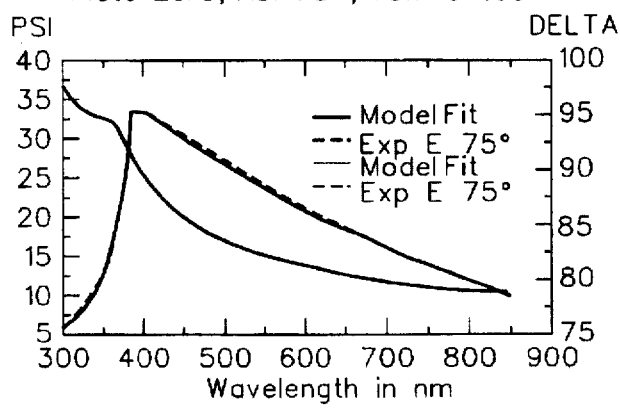
Figure 7C:
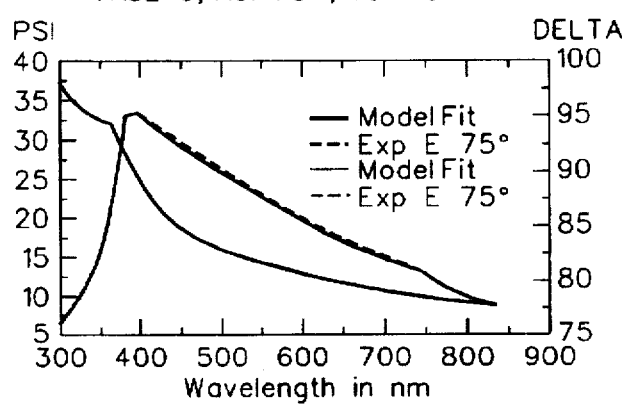
Figure 7D:
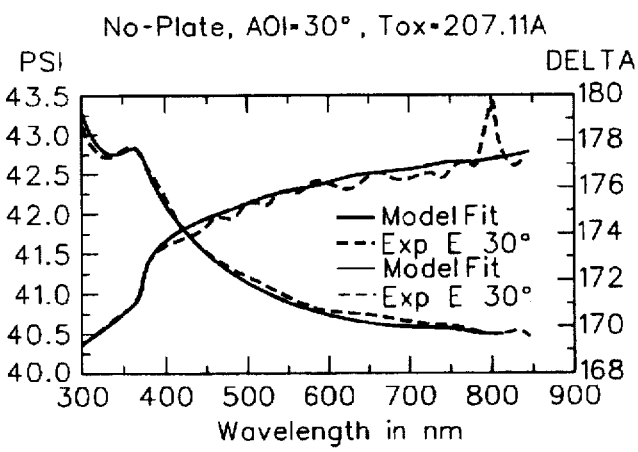
Figure 7E:
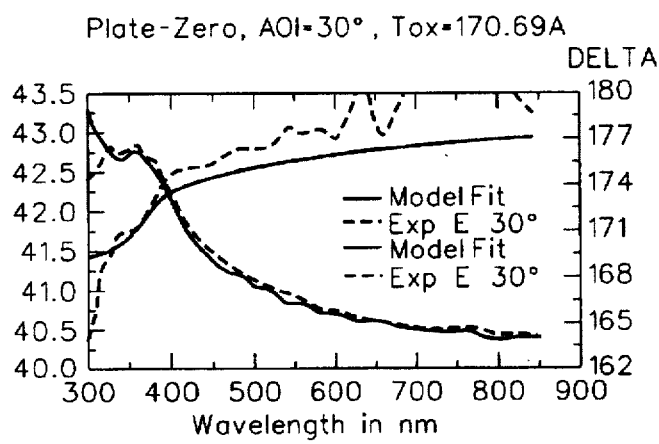
Figure 7F:
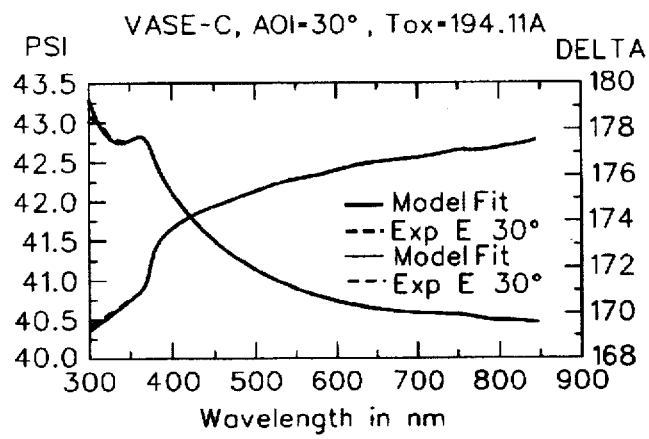

FIGS. 7a–7f show additional PSI and DELTA plots achieved from data acquired from various of the Modes identified above. FIGS. 7a–7c are for data acquired using an (AOI) of seventy-five (75) degrees, and FIGS. 7c–7f are plots achieved from data acquired using an (AOI) of thirty (30) degrees. FIG. 7a is for a Case 1 No-Plate Mode, FIG. 7b is for a Case 3 Plate-Zero Mode and FIG. 7c is for a Case 4 VASE-C Mode. Note that the PSI and DELTA values shown in FIGS. 7a–7c are all good. Note however, that the DELTA values shown in FIG. 7f is superior to that shown in FIGS. 7d and 7e. That is, where the (AOI) is set at thirty (30) degrees, only the Case 4 VASE-C approach to calculating DELTA provided a very good result over the full spectrum of wavelengths shown.

In view of the foregoing, it is to be understood that the most important results shown by said Inventors provided Test Results are:

1. Use of the Case 4 VC VASE-C Mode in evaluating PSI and DELTA parameters allows greatly reduced restraints on the Angle Of Incidence (AOI) of a Substrate Probing Polarized Beam of Light, (said (AOI) being with reference to the surface of a Sample System being investigated). That is, for instance, PSI and DELTA Values for a Semiconductor can be found by Regression on data obtained with the (AOI) at seventy-five (75) degrees, which is the Principal or Brewster Angle as is well known. With the present invention in place, however, the quality of data obtained with the (AOI) set to thirty (30) degrees, for instance, allows PSI and DELTA Value determination equally as well when a Case 4 VASE-C Mode approach is utilized. Again, this means that the (AOI) need not be set to the Principal or Brewster Angle to obtain high quality Data. Those knowledgeable in the field of Ellipsometry will immediately recognize the surprising nature of this result. (Note that the PSI and DELTA Values obtained at different (AOI's) are not the same Values, but that the Data obtained with the (AOI) set to thirty (30) degrees is of a quality associated with data taken at the Principal or Brewster Angle. Again, where a Semiconductor is the Sample System, the (AOI) is typically set at the Brewster Angle of approximately seventy-five (75) degrees, where DELTA is near ninety (90) degrees, and ellipsometric BETA becomes a minimum, (ideally zero (0.0), to obtain Data which allows reliable calculation Delta values. That is, Polarization State sensitivity to Sample Substrate Optical and Physical properties drops quickly when the (AOI) is varied from seventy-five (75) degrees. The present invention, however, allows use of an (AOI) of thirty (30) degrees, (and other (AOI's), with essentially no loss of said sensitivity. This is, as those experienced in the field of ellipsometry will immediately recognize, is surprising and significant, emphasis added.

2. Use of the Case 4 VASE-C Mode to measure DELTA Values where the (AOI) is near the angle at which DELTA quickly changes from near one-hundred-eighty (180) degrees to zero (0.0) degrees. The case investigated by the Inventors involved a thick BK7 Glass Sample System. The critical (AOI) is between fifty-six

(56) and fifty-eight (58) degrees. The very surprising result is that PSI and DELTA Data in the obtained regions from fifty-five (55) to fifty-six (56) degrees and from fifty-seven (57) to fifty-eight (58) degrees is sufficiently accurate to allow calculation of Thin Film roughness, losses, thickness and Optical Refractive Index therefrom. Those knowledgeable in the field of Ellipsometry will recognize the surprising nature of this as previously DELTA's associated with the identified (AOI) ranges were not measurable with sufficient accuracy using Rotating Element Ellipsometers (REE's), (eg. (RAE), (RPE) etc.).

It is felt that Patentable material is presented herein in both System and Method Categories. The System which allows multidirectional "Tilt" of Berek-type Retarder(s), which Retarders are positioned as described infra in Ellipsometer Systems, is considered new, novel, nonobvious and useful in the context of Ellipsometer Systems. For instance, the Inventors are unaware of any mounting system for a Berek-Type Variable Retarder which allows more than one direction of "Tilt" for use in any context. It is also felt that the Method of use of any Retarder System(s), which are Continuously Variable over a relatively large spectroscopic range of wavelengths, positioned as described infra, in Ellipsometer Systems to allow setting ellipsometric BETA in a range in which it is relatively insensitive to noise and errors in measurement etc. thereof, so that Transfer Functions which allow determination of PSI and DELTA from a measured ellipsometric ALPHA and ellipsometric BETA are not unusably sensitive to noise and errors in the measurement etc. of ellipsometric BETA, also meets the criteria for Patentability, (particularly where the Case 4 VASE-C Mathematical Regression approach to PSI and DELTA is utilized).

It is further felt that the use of a "Mathematical Regression" as applied to a multiplicity of ellipsometric ALPHA-ellipsometric BETA pair values, to arrive at PSI and DELTA values, is new, novel, nonobvious and useful. This is felt to be the case whether ellipsometric Beta value range control is utilized or not in obtaining ellipsometric BETA values. That is, whether a Case 2 No-Plate Regression or Case 4 VASE-C Mode, respectively is practiced. Also, as described infra, said Case 2 and Case 4 Modes utilizes well known "Mathematical Regression" approaches to arrive at PSI and DELTA values, provided an array of measured ellipsometric ALPHA and ellipsometric BETA values. Such can be considered as an "indirect", as opposed to a "direct" means for determining PSI and DELTA. In a "direct" approach singular ellipsometric ALPHA and ellipsometric BETA values are simply plugged directly into Eqs. 2 and 3, for instance, and PSI and DELTA simply calculated. A number of so directly determined PSI and DELTA values can be averaged, and the approach is still considered a "direct" approach. A regression approach, however, briefly, utilizes an array of ellipsometric ALPHA and ellipsometric BETA values, and finds PSI and DELTA values which correspond to a Least Mean or Least Square Error, for instance, "fit" to said ellipsometric ALPHA and Ellipsometric BETA data.

It is also believed that the capability of the present invention system to include one or more Variable Retarder(s) in an Ellipsometer System, the presence of which can be mad e essentially "transparent" to an end use by the multi-direction "Tilt" capability which allows alignment of an Incident Beam of Light essentially "exactly" with the Optical Axis of a Berek-Type Variable Retarder, is in itself strong evidence of Patentability. To date only one direction of "Tilt" has been possible with commercially available Berek-Type Variable Retarder mounting means. While one direction of "Tilt" can allow adjustment of a Variable Retarder sufficient for most applications, the present invention extended the capability of Ellipsometers generally, to allow degrees of precision not heretofore available. The present multi-tilt capability allows adjusting out the effect of imperfections in Retarder(s) (eg. out of parallel surfaces and bulk defects etc.), which imperfections vary from Variable Retarder to Variable Retarder as received from a manufacturer. That is, an Ellipsometer can be custom adjusted to eliminate imperfections resulting from imperfections vary from Variable Retarder to Variable Retarder.

Continuing, a Rotating Analyzer Ellipsometer (RAE) was used as an example in the foregoing, it is to be understood that the foregoing discussion is entirely applicable to Rotating Polarizer Ellipsometer (RPE) Systems where the functions of the Analyzer, (which becomes a nonrotating element (A)), and Polarizer, (which becomes a Rotating Polarizer (RP)), are simply reversed. That is, in a Rotating Polarizer Ellipsometer (RPE) there is present a Rotating Polarizer (RP) and an Analyzer (A), rotation of which Analyzer (A) sets its Azimuthal Angle which is the ellipsometric ALPHA determining parameter, (identified as ANL)), equivalent to (POL) in the foregoing. In a Rotating Analyzer Ellipsometer then, a Polarizer sets a Polarization State and a Rotating Analyzer analyzes changes in such effected by interaction with a Sample System. In a Rotating Polarizer Ellipsometer, the Rotating Polarizer sets an continuous array of Polarization States and a Station Analyzer interprets changes in such effected by interaction with a Sample System.

As well, while the equations corresponding to Eqs. 1, 2, 3 and 4, herein, (which corresponding equations are not presented herein), are somewhat different in other than Rotating Analyzer and Rotating Polarizer Ellipsometers, the foregoing discussion is generally applicable to any Ellipsometer System which contains a Rotating Element, (such as a Rotating Compensator Ellipsometer, a Rotating Analyzer and Polarizer and Fixed Compensator Ellipsometer).

Finally, it must also be mentioned that in the foregoing, Fourier Analysis has been cited as a typical approach to evaluation of ellipsometric ALPHA and ellipsometric BETA Values in EQ. 1. It is to be understood that ellipsometric ALPHA and ellipsometric BETA are representations of a modulated intensity superimposed upon a constant Intensity signal provided by an Ellipsometer Detector System (DET). It is possible to arrive at representations of said modulated Intensity by other than Fourier Analysis. For instance an approach which utilizes digitizing is known as "Hadamard" Analysis. As well, least or mean square error curve fitting approaches can be utilized. Methods known as "Simplex" and "Newton-Ralphson" are examples of such approaches. The ellipsometric ALPHA and ellipsometric BETA terms in the Claims are to be interpreted sufficiently broadly to include parameters arrived at by any such analysis approach, which parameters represent modulation of an intensity signal. Applicable mathematical approaches are described in numerous text books such as NUMERICAL RECIPES IN C, Cambridge University Press, 1988, said reference being incorporated by reference into this Disclosure.

Having hereby disclosed the subject matter of this invention, it should be obvious that many modifications, substitutions, and variations of the present invention are possible in view of the teachings. It is therefore to be understood that the invention may be practiced other than as specifically described, and should be limited in breadth and scope only by the Claims.

We claim:

1. An ellipsometer system which enables accurate and precise determination of PSI and DELTA values of essentially any investigatable sample system; said ellipsometer system comprising means for setting at least one polarization state in a beam of polarized light and means for identifying, and means for monitoring, a polarization state in said polarized beam of light, after an interaction thereof with a sample system;

between said means for setting at least one polarization state in a beam of polarized light and said means for monitoring a polarization state in said polarized beam of light, there being present at least one adjustable means for controlling an ellipsometric phase angle between orthogonal components in a polarized beam of light, which adjustable means for controlling an ellipsometric phase angle, in use, allows sequentially setting a plurality of ellipsometric phase angles between orthogonal components in a polarized beam of light which is caused by said ellipsometer system to interact with a sample system, such that in use said ellipsometric phase angle can be set sequentially through a plurality of settings while ellipsometric data is obtained by said means for monitoring a polarization state in said polarized beam of light at at least two selected settings of said at least one adjustable means for controlling an ellipsometric phase angle; which obtained ellipsometric data can be utilized in determination of PSI and DELTA values of an investigated sample system, where said determination of said PSI and DELTA values includes compensating for the effects on said obtained ellipsometric data of said at least two selected setting of said at least one adjustable means for controlling an ellipsometric phase angle, on said obtained ellipsometric data;

said ellipsometer system being further comprised of computational means which performs determination of investigated sample system PSI and DELTA values, which computational means utilizes data obtained with said at least one adjustable means for controlling ellipsometric phase angle between orthogonal components in a polarized beam of light, being set to at least two selected settings, and which computational means performs compensation of the effects of said at least one adjustable means for controlling ellipsometric phase angle between orthogonal components, on said utilized ellipsometric data obtained at said at least two selected settings of said at least one adjustable means for controlling ellipsometric phase angle between orthogonal components, in determining sample system PSI and DELTA values.

2. An Ellipsometer system as in claim 1, in which at least one selection from the group consisting of: (said means for setting at least one polarization state and said means for identifying a polarization state in said polarized beam of light), is an adjustable means for controlling an ellipsometric relative magnitude ratio of said orthogonal components, such that a plurality of ellipsometric relative magnitude ratios of said orthogonal components can be set thereby; and in which said computational means further performs compensation of any effects on obtained data resulting from adjustment(s) entered to ellipsometric relative magnitude ratios of said orthogonal components by said adjustable means for controlling an ellipsometric relative magnitude ratio of said orthogonal components in a polarized beam of light which is caused to interact with a sample system.

3. An ellipsometer system as in claim 2, in which said adjustable means for controlling an ellipsometric relative magnitude ratio of orthogonal components in a polarized beam of light comprises an adjustable polarizer.

4. An ellipsometer system as in claim 2, in which said adjustable means for controlling an ellipsometric relative magnitude ratio of orthogonal components in a polarized beam of light comprises an adjustable analyzer.

5. An ellipsometer system as in claim 1, in which said at least one adjustable means for controlling an ellipsometric phase angle between said orthogonal components in a polarized beam of light comprises a variable retarder.

6. An ellipsometer system as in claim 5, in which said variable retarder is Berek-type with its optical axis directed essentially perpendicular to a surface thereof, said Berek-type variable retarder being mounted in said ellipsometer system so as to allow it to be tilted about multiple axes thereby enabling it to provide variable amounts of retardance between orthogonal components in a beam of polarized light caused to pass therethrough, and so that optical axis can be caused to be aligned with said polarized beam of light with the result being that said Berek-type variable retarder becomes essentially end-user "transparent", without removal of said Berek-type variable retarder from said ellipsometer system.

7. An ellipsometer system as in claim 5, in which said variable retarder is selected from the group consisting of:

a system of at least two fixed-order-waveplate-type retarders which can be rotated with respect to one another, each about an axis perpendicular to an optical axes thereof, said optical axes being parallel to the surface of said fixed-order-waveplate-type retarders;

a Babinet dual wedge-type variable retarder;

a Soleil dual wedge-type variable retarder;

a Kerr electro-optical-type variable retarder;

a Pockels electro-optical-type variable retarder;

a liquid crystal electro-optical-type variable retarder;

a Voigt magnetic-faraday-effect variable retarder; and a Cotton-Mouton magnetic-faraday-effect variable retarder.

8. An Ellipsometer system as in claim 1, in which said at least one adjustable means for controlling an ellipsometric phase angle between said orthogonal components in a polarized beam of light has the capability of providing functional retardation between orthogonal components in a polarized beam of light over a spectroscopic range of at least two-hundred-thirty (230) to seventeen-hundred (1700) nanometers.

9. A Method of determination of sample system PSI and DELTA values with improved accuracy and precision comprising, in a functional order, the steps of:

providing an ellipsometer system which enables accurate and precise determination of PSI and DELTA values of essentially any investigatable sample system; said ellipsometer system comprising means for setting at least one polarization state in a beam of polarized light and means for identifying, and means for monitoring, a polarization state in said polarized beam of light, after an interaction thereof with a sample system;

between said means for setting at least one polarization state in a beam of polarized light and said means for monitoring a polarization state in said polarized beam of light, there being present at least one adjustable means for controlling an ellipsometric phase angle between orthogonal components in a polarized beam of light, which adjustable means for controlling an ellipsometric phase angle, in use, allows sequentially setting a plurality of ellipsometric phase angles between orthogonal components in a polarized beam of light which is caused by said ellipsometer system to interact with a sample system, such that in use said ellipsometric phase angle can be set sequentially through a plurality of settings while ellipsometric data is obtained by said means for monitoring a polarization state in said polarized beam of light at at least two selected settings of said at least one adjustable means for controlling an ellipsometric phase angle; which obtained ellipsometric data can be utilized in determination of PSI and DELTA values of an investigated sample system, where said determination of said PSI and DELTA values includes compensating for the effects on said obtained ellipsometric data of said at least two selected setting of said at least one adjustable means for controlling an ellipsometric phase angle, on said obtained ellipsometric data;

said ellipsometer system being further comprised of computational means which performs determination of investigated sample system PSI and DELTA values, which computational means utilizes data obtained with said at least one adjustable means for controlling ellipsometric phase angle between orthogonal components in a polarized beam of light, being set to at least two selected settings, and which computational means performs compensation of the effects of said at least one adjustable means for controlling ellipsometric phase angle between orthogonal components, on said utilized ellipsometric data obtained at said at least two selected settings of said at least one adjustable means for controlling ellipsometric phase angle between orthogonal components, in determining sample system PSI and DELTA values;

placing a sample system to be investigated into said ellipsometer system and causing a beam of polarized light from said means for setting at least one polarization state in a beam of polarized light to interact therewith and enter said means for monitoring a polarization state;

adjusting said at least one adjustable means for controlling ellipsometric phase angle between said orthogonal components to be sequentially set to a plurality of settings while ellipsometric data is obtained by said means for monitoring a polarization state in said polarized beam of light at at least two selected settings from said plurality settings of said at least one adjustable means for controlling a value of ellipsometric phase angle between said orthogonal components;

causing said computational means to determine investigated sample system PSI and DELTA values by a method which performs compensation of the effects of said at least one adjustable means for controlling ellipsometric phase angle between orthogonal components in a polarized beam of light on said ellipsometric data obtained at said at least two selected settings of said at least one adjustable means for controlling ellipsometric phase angle between orthogonal components in a polarized beam of light which is caused to interact with a sample system, in determining sample system PSI and DELTA values; and optionally determining at least some of members of the group consisting of: (the "Handedness", Stokes Vector, and Jones and Mueller Matrix components) of said polarized beam of light and investigated sample system.

10. A Method of determination of sample system PSI and DELTA values as in claim 9, in which data comprising a plurality of relative magnitude ratios of orthogonal components and phase angles between orthogonal components are obtained, at least some of which plurality of ellipsometric relative magnitude ratios of orthogonal components and measured ellipsometric phase angles between orthogonal components correspond to sequential adjusted settings of ellipsometric relative magnitude ratios of orthogonal components present in said beam of polarized light, said sequential adjusted settings being effected by adjustment of at least one member of the group consisting of: (said means for setting at least one polarization state in a beam of polarized light and said means for identifying a polarization state in said polarized beam of light); and in which said computational means is also caused to perform compensation of the effects of said sequential adjusted settings of ellipsometric relative magnitude ratios of orthogonal components present in said beam of polarized light which is caused by said ellipsometer system to interact with a sample system, in determining investigated sample system PSI and DELTA values.

11. A Method of determination of sample system PSI and DELTA values as in claim 10, in which a plurality of ellipsometric phase angles between orthogonal components are effected at each sequential adjusted setting of ellipsometric relative magnitude ratio of orthogonal components present in said beam of polarized light which is caused by said ellipsometer system to interact with a sample system.

12. A method of reducing the sensitivity of rotating analyzer ellipsometer (RAE) PSI and DELTA transfer functions to measured ellipsometric ALPHA and ellipsometric BETA parameter values which is applicable over spectroscopic range, which method enables acquiring data from a (RAE) system which is of an accuracy and precision which allows calculation of sample system PSI and DELTA, even where other than the Brewster angle of incidence (AOI) of a polarized beam of light to a sample system is utilized, and even where DELTA is near zero (0.0) or one-hundred-eighty (180) degrees, which method also enables determination of the "Handedness" of a beam of polarized light utilized in said RAE, said method comprising the steps of:

providing a (RAE) system which in use comprises:
a polarization state generator system comprising:
a source of a beam of light;
a means for setting a polarization state in said beam of light;
a sample system; and
a polarization state detector system comprising:
a rotating analyzer; and
a detector system;

which (RAE) further comprises at least one Berek-type variable retarder placed between said polarization state generator system, and said polarization state detector system; such that during use a beam of light is caused to exit said source of a beam of light, and have an ellipsometric ALPHA parameter determining state of polarization effected therein by said means for setting a polarization state; which polarized beam of light is caused to interact with said sample system, and with said at least one Berek-type variable retarder placed between said polarization state generator system and said polarization state detector system; which polarization state generator system can be adjusted to set a value of ellipsometric ALPHA and which said at least one Berek-type variable retarder can be tilted, so as to set a value of ellipsometric BETA parameter, such that said ellipsometric ALPHA and ellipsometric BETA are in ranges in which a transfer function which mediates determining DELTA from a measured ellipsometric ALPHA parameter and ellipsometric BETA parameter is relatively immune to noise and errors in measurement etc. of said ellipsometric BETA parameter;

causing a beam of light to exit said source of a beam of light, and causing an ellipsometric ALPHA setting state of polarization therein with said means for setting a polarization state;

causing said resulting polarized beam of light to interact with said sample system, and with said at least one Berek-type variable retarder placed between said polarization state generator system and said polarization state detector system, and with said polarization state detector system;

adjusting said means for setting a state of polarization to at least one setting and said at least one Berek-type variable retarder to, sequentially, a plurality of tilt settings while obtaining ellipsometric data;

and determining PSI and DELTA values utilizing said obtained ellipsometric ALPHA and ellipsometric BETA parameter values by a mathematical technique that compensates adjustments made to said means for setting a state of polarization and said at least one Berek-type variable retarder on measured ellipsometric ALPHA and ellipsometric BETA parameter values.

13. A method of reducing the sensitivity of rotating analyzer ellipsometer (RAE) PSI and DELTA transfer functions to measured ellipsometric ALPHA and ellipsometric BETA parameter values which is applicable over spectroscopic range, which method enables acquiring data from a (RAE) system which is of an accuracy and precision which allows calculation of sample system PSI and DELTA, even where other than the Brewster angle of incidence (AOI) of a polarized beam of light to a sample system is utilized, and even where DELTA is near zero (0.0) or one-hundred-eighty (180) degrees, which method also enables determination of the "Handedness" of a beam of polarized light utilized in said (RAE), said method comprising the steps of:

providing a (RAE) system which in use comprises:
      a polarization state generator system comprising:
         a source of a beam of light;
         a means for setting a polarization state in said beam of light;
      a sample system; and
      a polarization state detector system comprising:
         a rotating analyzer; and
         a detector system;
   which (RAE) further comprises at least one variable retarder selected from the group consisting of:
      a system of at least two fixed-order-waveplate-type retarders which can be rotated with respect to one another, each about an axis perpendicular to an optical axes thereof, said optical axes being parallel to the surface of said fixed-order-waveplate-type retarders;
      a Babinet dual wedge-type variable retarder;
      a Soleil dual wedge-type variable retarder;
      a Kerr electro-optical-type variable retarder;
      a Pockels electro-optical-type variable retarder;
      a liquid crystal electro-optical-type variable retarder;
      a Voigt magnetic-faraday-effect variable retarder; and
      a Cotton-Mouton magnetic-faraday-effect variable retarder;
      a Berek-type variable retarder;
   said at least one variable retarder being placed between said Polarization State generator system, through which said polarized beam of light must pass during use, and said Polarization State detector system;

causing a beam of light to exit said source of a beam of light, and causing an ellipsometric ALPHA setting state of polarization therein with said means for setting a polarization state;

causing said resulting polarized beam of light to interact with said sample system, and with said at least one variable retarder placed between said polarization state generator system and said polarization state detector system, adjustment of said variable retarder serving to set a value of said ellipsometric BETA parameter;

adjusting said means for setting a state of polarization to at least one setting and said at least one variable retarder to, sequentially, a plurality of settings while obtaining ellipsometric data;

and determining PSI and DELTA values utilizing said obtained ellipsometric ALPHA and ellipsometric BETA parameter values by a mathematical technique that compensates adjustments made to said means for setting a state of polarization and said at least one variable retarder on measured ellipsometric ALPHA and ellipsometric BETA parameter values.

14. A rotating analyzer ellipsometer system (RAE) comprising:
   a polarization state generator system comprising:
      a source of a beam of light;
      a means for setting a polarization state in said beam of light;
   a sample system; and
   a polarization state detector system comprising:
      a rotating analyzer; and
      a detector system;
which (RAE) further comprises at least one Berek-type variable retarder placed between said polarization state generator system, and said polarization state detector system; such that during use a beam of light is caused to exit said source of a beam of light, and have an ellipsometric ALPHA parameter determining state of polarization effected therein by said means for setting a polarization state; which polarized beam of light is caused to interact with said sample system, and with said at least one Berek-type variable retarder placed between said polarization state generator system and said polarization state detector system; which said at least one Berek-type variable retarder can be tilted so as to set a value of ellipsometric BETA parameter in a range in which a transfer function which mediates determining DELTA from a measured ellipsometric ALPHA parameter and ellipsometric BETA parameter is relatively immune to noise and errors in measurement etc. of said ellipsometric BETA parameter; said (RAE) being further comprised of computational means which performs said determination of said sample system PSI and DELTA, said determination of said sample system PSI and DELTA requiring input of data acquired with said ellipsometric BETA setting Berek-type variable retarder set in a plurality of tilt positions, which computational means compensates acquired data input thereto, for the effects of said required plurality of ellipsometric BETA setting Berek-type variable retarder tilts.

15. A rotating analyzer ellipsometer (RAE) system as in claim 14 in which the Berek-type variable retarder is mounted so as to simultaneously allow user directed tilt in more than one direction, said multiple tilt capability allowing a user to adjust said Berek-type retarder so that it has no effect, other than a negligible attenuation, on a beam of polarized light passing therethrough.

16. A rotating analyzer ellipsometer (RAE) system as in claim 14 which further comprises at least one additional element selected from the group consisting of:

a stationary polarizer;

a stationary analyzer;

a stationary compensator;

a rotating polarizer; and a rotating analyzer.

17. A rotating analyzer ellipsometer system (RAE) comprising:

a polarization state generator system comprising:
a source of a beam of light;
a means for setting a polarization state in said beam of light;

a sample system; and a polarization state detector system comprising;
a rotating analyzer; and
a detector system;

which (RAE) further comprises at least one variable retarder selected from the group consisting of:

a system of at least two fixed-order-waveplate-type retarders which can be rotated with respect to one another, each about an axis perpendicular to an optical axes thereof, said optical axes being parallel to the surface of said fixed-order-waveplate-type retarders;

a Babinet dual wedge-type variable retarder;

a Soleil dual wedge-type variable retarder;

a Kerr electro-optical-type variable retarder;

a Pockels electro-optical-type variable retarder;

a liquid crystal electro-optical-type variable retarder;

a Voigt magnetic-faraday-effect variable retarder;

a Cotton-Mouton magnetic-faraday-effect variable retarder; and a Berek-type variable retarder; such that in use said at least one variable retarder is placed between said polarization state generator system, and said polarization state detector system; such that during use a beam of light is caused to exit said source of a beam of light, and have an ellipsometric ALPHA parameter determining state of polarization effected therein by said means for setting a polarization state; which polarized beam of light is caused to interact with said sample system, and with said at least one variable retarder placed between said polarization state generator system and said polarization state detector system; which said at least one variable retarder can be adjusted so as to set a value of ellipsometric BETA parameter in a range in which a transfer function which mediates determining DELTA from a measured ellipsometric ALPHA parameter and ellipsometric BETA parameter is relatively immune to noise and errors in measurement etc. of said ellipsometric BETA parameter; said (RAE) being further comprised of computational means which performs said determination of said sample system PSI and DELTA, said determination of said sample system PSI and DELTA requiring input of data acquired with said ellipsometric BETA setting variable retarder set in a plurality of positions, which computational means compensates acquired data input thereto, for the effects of said required plurality of ellipsometric BETA setting variable retarder positions.

18. A rotating analyzer ellipsometer (RAE) system as in claim 17 which further comprises at least one additional element selected from the group consisting of:

a stationary polarizer;

a stationary analyzer;

a stationary compensator;

a rotating polarizer; and a rotating analyzer.

19. A method of determining sample system PSI and DELTA values by use of a rotating analyzer ellipsometer (RAE) system, comprising the steps of:

providing an (RAE) system which comprises:
a polarization state generator system comprising:
a source of a beam of light;
a means for setting a polarization state in said beam of light;
a sample system effectively comprised of a sample system per se. and a variable retarder; and
a polarization state detector system comprising;
a rotating analyzer; and
a detector system;

which method further comprises the steps of:

measuring a plurality of sample system ellipsometric ALPHA and ellipsometric BETA parameter pairs, as a function of at least one means for setting a polarization state in said beam of light setting(s), and a plurality of variable retarder settings; and applying a mathematical technique to said plurality of measured ellipsometric ALPHA and ellipsometric BETA parameter pairs to determine PSI and DELTA values for said sample system per se. while compensating for the presence of said variable retarder.

20. A method of determining sample system PSI and DELTA values by use of a rotating analyzer ellipsometer (RAE) system, comprising the step of:

providing an (RAE) system comprising:
a polarization state generator system comprising:
a source of a beam of light;
a means for setting a polarization state in said beam of light;
a sample system; and
a polarization state detector system comprising;
a rotating analyzer; and
a detector system;

which (RAE) system further comprises a Berek-type variable retarder placed between said polarization state generator system, and said polarization state detector system; such that during use said Berek-type variable retarder can be tilted so as to set a value of an ellipsometric BETA parameter in a range in which a transfer function which mediates determining DELTA from a measured ellipsometric ALPHA parameter and ellipsometric BETA parameter is relatively immune to noise and errors in measurement etc. of said ellipsometric BETA parameter, which method further comprises the steps of:

measuring a plurality of sample system ellipsometric ALPHA and ellipsometric BETA parameter pairs corresponding to, at each of at least one means for setting a polarization state in said beam of light setting(s), and at least five Berek-type retarder settings, said Berek-type retarder settings including no-tilt, clockwise and counterclockwise elevational, and clockwise and counterclockwise azimuthal tilts; and applying a mathematical technique to said plurality of measured ellipsometric ALPHA and ellipsometric BETA parameter pairs to determine sample system PSI and DELTA values, while compensating for presence of said at least one Berek-type variable retarder.

21. A method of determining sample system PSI and DELTA values by use of a rotating analyzer ellipsometer (RAE) system, comprising the step of:

providing an (RAE) system comprising
a polarization state generator system comprising:
a source of a beam of light;
a means for setting a polarization state in said beam of light;
a sample system; and
a polarization state detector system comprising:
a rotating analyzer; and
a detector system;

which (RAE) system further comprises at least one variable retarder selected from the group consisting of:

a system of at least two fixed-order-waveplate-type retarders which can be rotated with respect to one another, each about an axis perpendicular to an optical axes thereof, said optical axes being parallel to the surface of said fixed-order-waveplate-type retarders;

a Babinet dual wedge-type variable retarder;

a Soleil dual wedge-type variable retarder;

a Kerr electro-optical-type variable retarder;

a Pockels electro-optical-type variable retarder;

a liquid crystal electro-optical-type variable retarder;

a Voigt magnetic-faraday-effect variable retarder; and a Cotton-Mouton magnetic-faraday-effect variable retarder;

a Berek-type variable retarder;

said at least one variable retarder being placed between said polarization state generator system, and said polarization state detector system; such that during use said at least one variable retarder can be adjusted so as to set a value of ellipsometric BETA parameter in a range in which a transfer function which mediates determining DELTA from a measured ellipsometric ALPHA parameter and ellipsometric BETA parameter is relatively immune to noise and errors in measurement etc. of ellipsometric BETA parameter;

which method further comprises the steps of:

measuring a plurality of sample system ellipsometric ALPHA and ellipsometric BETA parameter pairs as a function of at least one means for setting a polarization state in said beam of light setting(s), and a plurality of variable retarder settings; and applying a mathematical technique to said plurality of measured ellipsometric ALPHA and ellipsometric BETA parameter pairs to determine sample system PSI and DELTA values, while compensating for the presence of said at least one variable retarder.

22. A method of reducing the sensitivity of rotating polarizer ellipsometer (RPE) PSI and DELTA transfer functions to measured ellipsometric ALPHA and ellipsometric BETA parameter values which is applicable over spectroscopic range, which method enables acquiring data from a (RPE) system which is of an accuracy and precision which allows calculation of sample system PSI and DELTA, even where other than the Brewster angle of incidence (AOI) of a polarized beam of light to a sample system is utilized, and even where DELTA is near zero (0.0) or one-hundred-eighty (180) degrees, which method also enables determination of the "Handedness" of a beam of polarized light utilized in said (RPE), said method comprising the steps of:

providing a (RPE) system which in use comprises:
a polarization state generator system comprising:
a source of a beam of light;
a rotating polarizer;
a sample system; and
a polarization state detector system comprising:
means for identifying a polarization state in said beam of light; and
a detector system;

which (RPE) further comprises at least one Berek-type variable retarder placed between said polarization sate generator system, and said polarization state detector system; such that during use a beam of light is caused to exit said source of a beam of light, and pass through said rotating polarizer in said polarization state generator and emerge as a series of polarization states; which beam of light in a series of polarization states is caused to interact with said sample system, and with said at least one Berek-type variable retarder placed between said polarization state generator system and said polarization state detector system; which at least one Berek-type variable retarder can be tilted so as to set a value of an ellipsometric BETA parameter in a range in which a transfer function which enables determining DELTA from a measured ellipsometric ALPHA parameter and ellipsometric BETA parameter is relatively immune to noise and errors in measurement etc. of said ellipsometric BETA parameter;

causing a beam of light to exit said source of a beam of light, pass through and emerge from said rotating polarizer in a series of polarization states;

causing said resulting beam of light in a series of polarization states to interact with said sample system, with said at least one Berek-type variable retarder placed between said polarization state generator system and said polarization state detector system and which serves to set a value of said ellipsometric BETA parameter, and with said means for identifying a state of polarization which serves to set a value of said ellipsometric ALPHA parameter;

adjusting said means for identifying a state of polarization to at least one setting and said at least one Berek-type variable retarder to, sequentially, a plurality of tilt settings while obtaining ellipsometric data;

and determining PSI and DELTA values utilizing said obtained ellipsometric ALPHA and ellipsometric BETA parameter values by a mathematical technique that compensates adjustments made to said means for identifying a state of polarization and said at least one Berek-type variable retarder in said measured ellipsometric ALPHA and ellipsometric BETA parameter values.

23. A method of reducing the sensitivity of rotating polarizer ellipsometer (RPE) PSI and DELTA transfer functions to measured ellipsometric ALPHA and ellipsometric BETA parameter values which is applicable over spectroscopic range, which method enables acquiring data from a (RPE) system which is of an accuracy and precision which allows calculation of sample system PSI and DELTA, even where other than the Brewster angle of incidence (AOI) of a polarized beam of light to a sample system is utilized, and even where DELTA is near zero (0.0) or one-hundred-eighty (180) degrees, which method also enables determination of the "Handedness" of a beam of polarized light utilized in said (RPE), said method comprising the steps of:

providing a (RPE) system which in use comprises:
a polarization state generator system comprising:
a source of a beam of light;
a rotating polarizer;
a sample system; and
a polarization state detector system comprising:
means for identifying a polarization state in said beam of light; and a detector system;
which (RPE) system further comprises at least one variable retarder selected from the group consisting of:

a system of at least two fixed-order-waveplate-type retarders which can be rotated with respect to one another, each about an axis perpendicular to an optical axes thereof, said optical axes being parallel to the surface of said fixed-order-waveplate-type retarders;

a Babinet dual wedge-type variable retarder;

a Soleil dual wedge-type variable retarder;

a Kerr electro-optical-type variable retarder;

a Pockels electro-optical-type variable retarder;

a liquid crystal electro-optical-type variable retarder;

a Voigt magnetic-faraday-effect variable retarder; and a Cotton-Mouton magnetic-faraday-effect variable retarder;

a Berek-type retarder;

said at least one variable retarder being placed between said polarization state generator system, through which said polarized beam of light must pass during use, and said polarization state detector system;

causing a beam of light to exit said source of a beam of light, pass through and emerge from said rotating polarizer in a series of polarization states;

causing said resulting beam of light in a series of polarization states to interact with said sample system, with said at least one variable retarder placed between said polarization state generator system and said polarization state detector system and which serves to set a value of said ellipsometric BETA parameter, and with said means for identifying a state of polarization which serves to set a value of said ellipsometric ALPHA parameter;

adjusting said means for identifying a state of polarization to at least one setting and said at least one variable retarder to, sequentially, a plurality of settings while obtaining ellipsometric data;

and determining PSI and DELTA values utilizing said obtained ellipsometric ALPHA and ellipsometric BETA parameter values by a mathematical technique that compensates adjustments made to said means for identifying a state of polarization and said at least one variable retarder in said measured ellipsometric ALPHA and ellipsometric BETA parameter values.

24. A rotating polarizer ellipsometer system (RPE) comprising:

a polarization state generator system comprising:
        a source of a beam of light;
        a rotating polarizer;

a sample system; and a polarization state detector system comprising;:
        means for identifying a polarization state in said beam of light; and
        a detector system;

which (RPE) further comprises at least one Berek-type variable retarder placed between said polarization state generator system, and said polarization state detector system; such that during use a beam of light is caused to exit said source of a beam of light, and pass through said rotating polarizer in said polarization state generator and emerge as in a series of polarization states; which beam of light in a series of polarization states is caused to interact with said sample system, and with said at least one Berek-type variable retarder placed between said polarization state generator system and said polarization state detector system; which at least one Berek-type variable retarder can be tilted so as to set a value of an ellipsometric BETA parameter in a range in which a transfer function which enables determining DELTA from a measured ellipsometric ALPHA parameter and ellipsometric BETA parameter is relatively immune to noise and errors in measurement etc. of said ellipsometric BETA parameter; said (RPE) being further comprised of computational means which performs said determination of said sample system PSI and DELTA, said determination of said sample system PSI and DELTA requiring input of data acquired with said ellipsometric BETA setting Berek-type variable retarder set in a plurality of tilt positions, which computational means compensates acquired data input thereto, for the effects of said required plurality of ellipsometric BETA setting Berek-type variable retarder tilts.

25. A rotating polarizer ellipsometer (RPE) system as in claim 24 in which the Berek-type variable retarder is mounted so as to simultaneously allow user directed tilt in more than one direction, said multiple tilt capability allowing a user to adjust said Berek-type retarder so that it has no effect, other than a negligible attenuation, on a beam of polarized light passing therethrough.

26. A rotating polarizer ellipsometer (RPE) system as in claim 24 which further comprises at least one additional element selected from the group consisting of:

a stationary polarizer;

a stationary analyzer;

a stationary compensator;

a rotating polarizer; and a rotating analyzer.

27. A rotating polarizer ellipsometer system (RPE) comprising:

a polarization state generator system comprising:
        a source of a beam of light;
        a rotating polarizer;

a sample system; and a polarization state detector system comprising:
        means for identifying a polarization state in said beam of light; and
        a detector system;

which (RPE) further comprises at least one variable retarder selected from the group consisting of:

a system of at least two fixed-order-waveplate-type retarders which can be rotated with respect to one another, each about an axis perpendicular to an optical axes thereof, said optical axes being parallel to the surface of said fixed-order-waveplate-type retarders;

a Babinet dual wedge-type variable retarder;

a Soleil dual wedge-type variable retarder;

a Kerr electro-optical-type variable retarder;

a Pockels electro-optical-type variable retarder;

a liquid crystal electro-optical-type variable retarder;

a Voigt magnetic-faraday-effect variable retarder;

a Cotton-Mouton magnetic-faraday-effect variable retarder; and a Berek-type variable retarder;

said at least one variable retarder being placed between said polarization state generator system, and said polarization state detector system; such that during use a beam of light is caused to exit said source of a beam of light, and pass through said rotating polarizer in said polarization state generator and emerge as in a series of polarization states; which beam of light in a series of polarization states is caused to interact with said sample system, and with said at least one variable retarder placed between said polarization state generator system and said polarization state detector system; which at least one variable retarder can be adjusted so as to set a value of an ellipsometric BETA parameter in a range in which a transfer function which enables determining DELTA from a measured ellipsometric ALPHA parameter and ellipsometric BETA parameter is relatively immune to noise and errors in measurement etc. of said ellipsometric BETA parameter; said (RPE) being further comprised of computational means which performs said determination of said sample system PSI and DELTA, said determination of said sample system PSI and DELTA requiring input of data acquired with said ellipsometric BETA setting variable retarder set in a plurality of positions, which computational means compensates acquired data input thereto, for the effects of said required plurality of ellipsometric BETA setting variable retarder positions.

28. A rotating polarizer ellipsometer (RPE) system in claim 27 which further comprises at least one additional element selected from the group consisting of:
    a stationary polarizer;
    a stationary analyzer;
    a stationary compensator;
    a rotating polarizer; and
    a rotating analyzer.

29. A method of determining sample system PSI and DELTA values by use of a rotating polarizer ellipsometer (RPE) system, comprising the step of:
    providing a (RPE) system comprising:
        a polarization state generator system comprising:
            a source of a beam of light;
            a rotating polarizer;
        a sample system effectively comprised of a sample system per se. and a variable retarder; and
        a polarization state detector system comprising:
            a means for identifying a polarization state in said beam of light;
            a detector system;
    which method further comprises the steps of:
        measuring a plurality of sample system ellipsometric ALPHA and ellipsometric BETA parameter pairs as a function of at least one means for identifying a polarization state in said beam of light setting(s), and a plurality of variable retarder settings; and
        applying a mathematical technique to said plurality of measured ellipsometric ALPHA and ellipsometric BETA parameter pairs to determine PSI and DELTA values for said sample system per se. while compensating for the presence of said variable retarder.

30. A method of determining sample system PSI and DELTA values by use of a rotating polarizer ellipsometer (RPE) system, comprising the step of:
    providing an (RPE) system comprising:
        a polarization state generator system comprising:
            a source of a beam of light;
            a rotating polarizer;
        a sample system; and
        a polarization state detector system comprising:
            a means for identifying a polarization state in said beam of light; and
            a detector system;
    which (RPE) system further comprises a Berek-type variable retarder placed between said polarization state generator system, and said polarization state detector system; such that during use said Berek-type variable retarder can be tilted so as to set a value of ellipsometric BETA parameter in a range in which a transfer function which enables determining DELTA from a measured ellipsometric ALPHA parameter and ellipsometric BETA parameter is relatively immune to noise and errors in measurement etc. of ellipsometric BETA parameter;

which method further comprises the steps of:
        measuring a plurality of sample system ellipsometric ALPHA and ellipsometric BETA parameter pairs corresponding to, at each of at least one means for identifying a polarization state in said beam of light setting(s), and at least five Berek-type retarder settings, said Berek-type retarder settings including no-tilt, clockwise and counterclockwise elevational, and clockwise and counterclockwise azimuthal tilts; and
        applying a mathematical technique to said plurality of measured ellipsometric ALPHA and ellipsometric BETA parameter pairs to determine sample system PSI and DELTA values, while compensating for the presence of said at least one Berek-type variable retarder.

31. A method of determining sample system PSI and DELTA values by use of a rotating polarizer ellipsometer (RPE) system, comprising the step of:
    providing an (RPE) system comprising:
        a polarization state generator system comprising:
            a source of a beam of light;
            a rotating polarizer;
        a sample system; and
        a polarization state detector system comprising:
            a means for identifying a polarization state in said beam of light;
            a detector system;
    which (RPE) system further comprises at least one variable retarder selected from the group consisting of
        a system of at least two fixed-order-waveplate-type retarders which can be rotated with respect to one another, each about an axis perpendicular to an optical axes thereof, said optical axes being parallel to the surface of said fixed-order-waveplate-type retarders;
        a Babinet dual wedge-type variable retarder;
        a Soleil dual wedge-type variable retarder;
        a Kerr electro-optical-type variable retarder;
        a Pockels electro-optical-type variable retarder;
        a liquid crystal electro-optical-type variable retarder;
        a Voigt magnetic-faraday-effect variable retarder; and
        a Cotton-Mouton magnetic-faraday-effect variable retarder;
        a Berek-type variable retarder;
    said at least one variable retarder being placed between said polarization state generator system, and said polarization state detector system; such that during use said at least one variable retarder can be adjusted so as to set a value of ellipsometric BETA parameter in a range in which a transfer function which enables determining DELTA from a measured ellipsometric ALPHA parameter and ellipsometric BETA parameter is relatively immune to noise and errors in measurement etc. of ellipsometric BETA parameter;

which method further comprises the steps of:
        measuring a plurality of sample system ellipsometric ALPHA and ellipsometric BETA parameter pairs as a function of at least one means for identifying a polarization state in said beam of light setting(s), and a plurality of variable retarder settings; and
        applying a mathematical technique to said plurality of measured ellipsometric ALPHA and ellipsometric BETA parameter pairs to determine sample system PSI and DELTA values while compensating for the presence of said at least one variable retarder.

* * * * *